United States Patent
Morozov et al.

(10) Patent No.: US 7,824,927 B2
(45) Date of Patent: Nov. 2, 2010

(54) ANALYTE DETECTION USING AN ACTIVE ASSAY

(75) Inventors: Victor Morozov, Manassas, VA (US); Charles L. Bailey, Cross Junction, VA (US); Melissa R. Evanskey, Potomac Falls, VA (US)

(73) Assignee: George Mason Intellectual Properties, Inc., Fairfax, VA (US)

( * ) Notice: Subject to any disclaimer, the term of this patent is extended or adjusted under 35 U.S.C. 154(b) by 0 days.

(21) Appl. No.: 11/397,905

(22) Filed: Apr. 5, 2006

(65) Prior Publication Data
US 2006/0263904 A1    Nov. 23, 2006

Related U.S. Application Data

(60) Provisional application No. 60/668,062, filed on Apr. 5, 2005.

(51) Int. Cl.
*G01N 33/549* (2006.01)
*C12M 3/00* (2006.01)

(52) U.S. Cl. .......................... 436/532; 435/2; 435/7.1; 435/285.2; 435/286.1; 435/286.2; 435/286.5; 435/287.2; 436/517; 436/518; 436/524; 436/528; 436/534; 436/538; 436/165; 436/177; 436/178

(58) Field of Classification Search .............. 435/4, 435/6, 7.1, 287.1, 287.2, 2, 285.2, 286.1, 435/286.2, 286.5, 517, 518, 524, 528, 532, 435/534, 538, 165, 177, 178; 436/501, 518, 436/528, 164, 174, 175, 177, 178, 807
See application file for complete search history.

(56) References Cited

U.S. PATENT DOCUMENTS

| | | | |
|---|---|---|---|
| 6,007,999 A * | 12/1999 | Clark | 435/7.1 |
| 6,245,508 B1 * | 6/2001 | Heller et al. | 435/6 |
| 6,270,672 B1 * | 8/2001 | Turecek et al. | 210/645 |
| 6,589,749 B1 * | 7/2003 | Guirguis | 435/7.2 |
| 7,189,322 B2 * | 3/2007 | Wu et al. | 210/321.77 |
| 2002/0153322 A1 * | 10/2002 | Bruening et al. | 210/659 |
| 2003/0089666 A1 * | 5/2003 | Bruening et al. | 210/681 |
| 2004/0115709 A1 * | 6/2004 | Morozov et al. | 435/6 |
| 2004/0198849 A1 * | 10/2004 | Aminabhavi et al. | 521/27 |
| 2004/0261508 A1 * | 12/2004 | Berndt | 73/61.79 |
| 2005/0009066 A1 * | 1/2005 | Connolly | 435/6 |
| 2005/0124077 A1 * | 6/2005 | Cole et al. | 436/518 |
| 2006/0073610 A1 * | 4/2006 | Kopaciewicz | 436/518 |

FOREIGN PATENT DOCUMENTS

WO    WO97/44651    * 11/1997

* cited by examiner

*Primary Examiner*—Gailene R Gabel
(74) *Attorney, Agent, or Firm*—David Yee; Edgar Rodriguez

(57) ABSTRACT

Analytes using an active assay may be detected by introducing an analyte solution containing a plurality of analytes to a lacquered membrane. The lacquered membrane may be a membrane having at least one surface treated with a layer of polymers. The lacquered membrane may be semi-permeable to nonanalytes. The layer of polymers may include cross-linked polymers. A plurality of probe molecules may be arrayed and immobilized on the lacquered membrane. An external force may be applied to the analyte solution to move the analytes towards the lacquered membrane. Movement may cause some or all of the analytes to bind to the lacquered membrane. In cases where probe molecules are presented, some or all of the analytes may bind to probe molecules. The direction of the external force may be reversed to remove unbound or weakly bound analytes. Bound analytes may be detected using known detection types.

12 Claims, 32 Drawing Sheets

Initial surface

BSA/GA layer in contact witmica

ANALYTE DETECTION USING AN ACTIVE ASSAY

CROSS REFERENCE TO RELATED APPLICATIONS

The present application claims the benefit of provisional patent application Ser. No. 60/668,062 to Morozov et al., filed on Apr. 5, 2005, entitled "Active Assay Techniques," which is hereby incorporated by reference.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of DOE Grant No. DE-F C52-04NA25455 awarded by the U.S. Department of Energy.

BACKGROUND OF THE INVENTION

There are several known techniques to assay viruses, bacterial cells and spores in environmental samples. The techniques may also be applied to biological fluids. Overall, they may be divided into three main categories.

The first category involves direct visualization of pathogens by direct optical, electron microscopy or atomic force microscopy. The second category involves detecting specific genes or oligonucleotide sequences after polymerase chain reaction (PCR) amplification. The third category involves common methods in assay of pathogens based on the use of pathogen-specific antibodies. This third type may employ various techniques, such as radioimmunoassay (RIA), enzyme-linked immunosorbant assay (ELISA), immunofluorescent microscopy, etc.

Sensitivity of all known detection methods may depend on the efficiency of pathogen collection, as well as the level of sensitivity of the detection method. Generally, as the level of sensitivity demanded increases, the sample volume decreases. In essence, when the pathogen concentration is low, deposition of pathogens may become more difficult.

Take, for instance, electron microscopy, where the total microscope grid size (S) can be approximately 3-5 mm$^2$. While such grid can float over a large sample volume, the surface density of particles in T seconds can be denoted by $$N/S \sim C(DT)^{1/2} \qquad (1)$$

where N represents the total number of bound particles, S represents the total open (viewable) area of a microscope grid, C represents the pathogen concentration, D represents the diffusion coefficient of the particles in solution, and T represents time.

D can be low for even for relatively small pathogens, such as viruses. For example, D can be $10^{-12}$ m$^2$/sec for virus particles. In this case, it can take a long time to accumulate sufficient density of bound viruses. Thus, to have at least one pathogen per square micron captured in, for example, 30 min., C may need to exceed $2 \times 10^{10}$ particles/mL. This pathogen concentration may be needed to overcome diffusion limitation, no matter how large the sample volume is. If the sample volume is 1 mL, then approximately $5 \times 10^6$ particles out of $2 \times 10^{10}$ particles may be captured under these conditions.

Atomic force microscopy (AFM) can present another challenge to sensitivity increase. Although it has the ability to detect single viruses, one would probably need to have at least $10^6$ viruses/mL to be able to image a few viral particles in a $5 \times 5$ μm$^2$ image suitable for observation. In contrast to electron microscopy, relatively slow scanning in AFM does not tend to allow one to quickly search a large area.

Single particle sensitivity has also been introduced using other techniques. For example, conductivity of a gap between two nanowires was shown to be sensitive to the binding of a single viral particle. However, similar to the above microscopy techniques, this technique usually works only with highly concentrated solutions when particles could appear on a small stage between the nanowires in a reasonably short time.

In essence, a major limitation with all known detection techniques that are sensitive to a single pathogen is that single pathogens are hard to bring to view when pathogens are spread within highly diluted solutions or suspensions.

An approach to overcome this limitation is preconcentrating the samples. This procedure is common in environmental analyses. However, additional preconcentration prolongs analysis and tends to be costly.

DETAILED DESCRIPTION

The disclosure embodies an active assay concept that provides for early detection of pathogens and pathogen-specific antibodies. In particular, a specially prepared semi-permeable membrane having a smooth surface may be prepared and used to electrophoretically capture pathogens that are actively delivered.

The disclosure also embodies different specific realizations of the active assay concept. For example, early humoral response molecules, such as immunoglobulin M (IgM), may be detected in a patient's serum as an indication of infection when the infection does not reveal any symptom. Another embodiment includes actively capturing pathogens coated with antibodies (both specific and nonspecific) onto an array of anti-antibody molecules. In yet another embodiment, antibody molecules or Fc receptors may allow diffusing over the substrate surface while being anchored. The latter typically allows the binding of immunoglobulin G (IgG)-coated pathogens while avoiding the binding of separate free IgG molecules.

Figure 1:
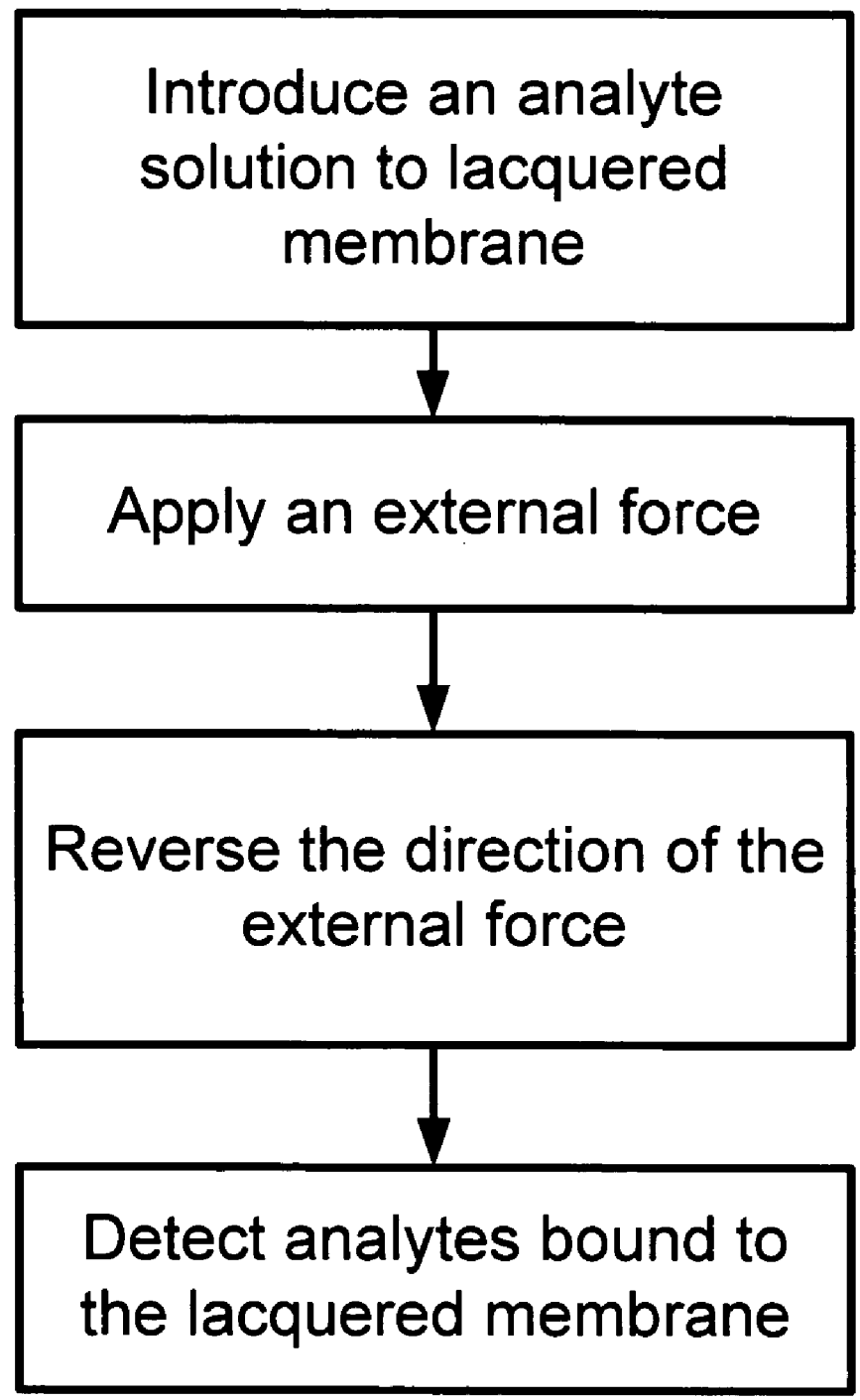
FIG. 1 shows an example of a flow diagram for detecting an analyte using an active assay.

Referring to FIG. 1, a method for detecting an analyte using an active assay is shown. In this method, an analyte solution may be introduced to a lacquered membrane. The analyte solution may contain a plurality of analytes, including but not limited to, pathogens, pathogen-specific antibodies, spores, fungi, etc. Pathogens include, but are not limited to, bacteria, viruses, fungi, bacteriophages, etc. The solution may be water based, including salt, sugars, polymers, detergents, buffer components, a combination thereof, etc.

The lacquered membrane may be any membrane, such as a dialysis membrane or any other membrane substrate. Examples of a membrane substrate include glass, gel, etc. Moreover, the lacquered membrane may be porous and have semi-permeable and/or ultra-filtration properties. Semi-permeability/ultra-filtration may aid in filtering nonanalytes (e.g., salt ions, buffer ions, etc.) through the membrane.

To create the lacquered membrane, at least one surface of the membrane may be treated with a layer of polymers. The layer, generally thin, may help smooth the roughness of the surface of the membrane without affecting the substrate's ultra-filtration properties. Smoothing may be achieved by flattening the layer. Flattening may be achieved by surface tension, by contact with a second smooth surface, the use of a roller, etc.

Polymers may be an assortment of cross-linked polymers. For instance, as one embodiment, these cross-linked polymers may be cross-linked water soluble polymers. In particular, these cross-linked water soluble polymers may be a family of globular proteins, such as Bovine Serum Albumin (BSA), egg albumen (OVA), hemoglobin, myoglobin, insulin, serum globulin in blood, enzymes, etc. Other cross-linked polymers include, but are not limited to, fibrous polymers such as gelatin (e.g., gelatin A, gelatin B, etc.) chitosan, dextran, and nucleic acids.

An external force may be applied to the analyte solution to move the analytes towards the lacquered membrane. Examples of external forces include, but are not limited to, electrical, mechanical, gravitational, centrifugal, hydrodynamic, pressure, etc. Using the enhanced properties of the dialysis membrane or membrane substrate, analytes may bind to the lacquered membrane. For instance, some analytes may bind to a carboxyl group of a cross-linked polymer. Generally, the external force may run as long as necessary (e.g., seconds, minutes, hours, etc.) to concentrate and capture analytes from diluted suspensions.

The external force and the semi-permeability/ultra-filtration properties of the lacquered membrane may assist in reducing salt concentration in the analyte solution. This reduction may be achieved through dialysis or electro-dialysis. Consequently, nonanalytes penetrating through the semi-permeable membrane may help lower the nonanalyte concentration in the solution, and thus permit a more effective detection, recognition and/or analysis of analytes.

After analytes have had some time to collect on the lacquered membrane, the direction of the external force is reversed. Reversal of force may result in the removal of unbound analytes or analytes that are weakly bound. The reversed force may be large enough to break unspecific bonds (e.g., weakly bound analytes, bound debris, etc.) but smaller than that needed to break specific bonds (e.g., bound analytes). The reversed force may also be larger than that required to break bonds between cross-reacting antigen-antibody pairs. Those that are removed may be laterally diffused, which permits the possibility of unbound analytes to bind to some other area on the lacquered membrane. Such removal may reduce background noise and increase assay sensitivity and specificity.

Analytes bound to the lacquered membrane may be detected, imaged and/or quantified using various methods. Detection techniques include, but are not limited to, AFM, RIA, ELISA and detection using functionalized magnetic and non-magnetic beads. Hence, if the selected detection method is AFM, analytes imaged may be achieved by, inter alia, (1) identifying certain morphological features (e.g., filamentous, spherical, etc.); (2) determining analyte size; (3) visualizing pili, flagella, cellular debris, and other impurities; (4) determining the total number of analytes in a pure sample, etc.

Figure 2:
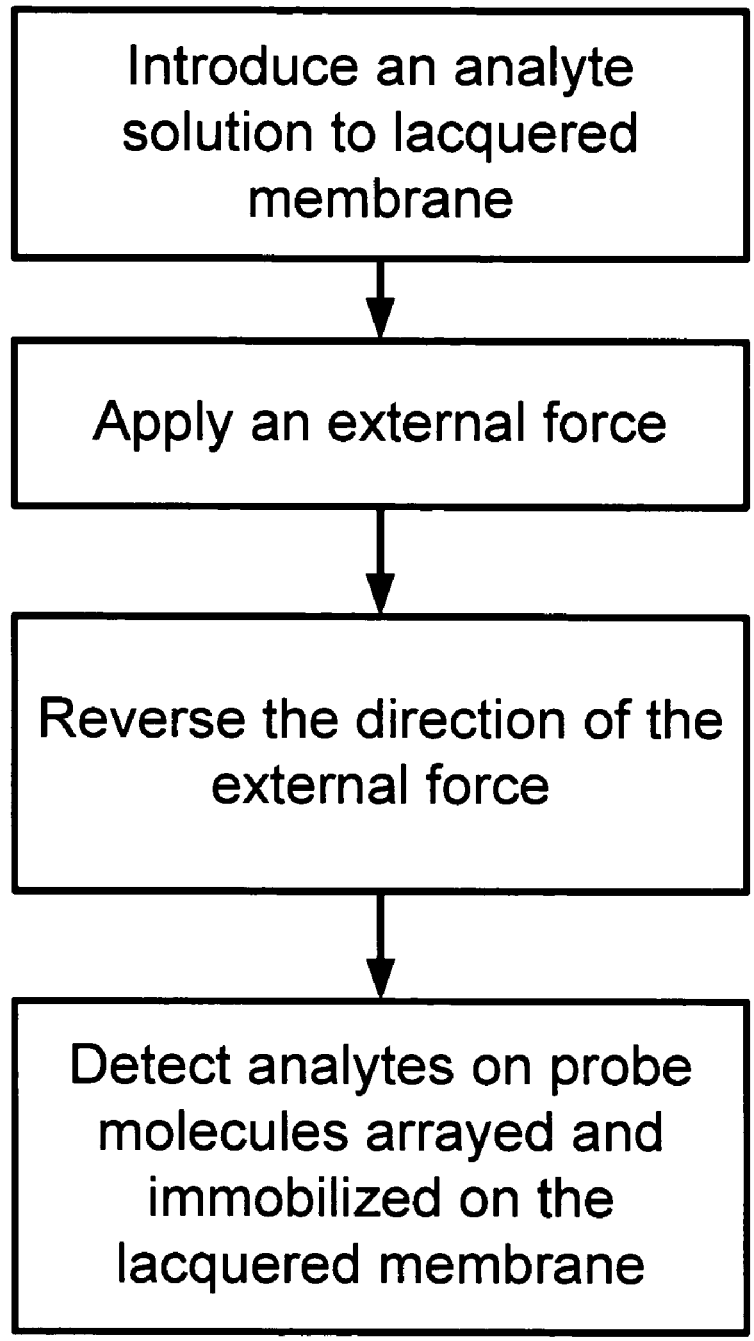
FIG. 2 shows a flow diagram of an embodiment of capturing analytes.

FIG. 2 shows an embodiment of capturing analytes. Here, a plurality of probe molecules may be introduced (e.g., deposition via electrospray, microspotting, ink-jetting, microcontact printing, etc.) on the lacquered membrane. This introduction may result in a microarray of probe molecules that are arrayed and immobilized on the lacquered membrane.

Probe molecules are molecules that serve as the binding sites for the analytes. These molecules may have an affinity for analytes or markers that can attach to the analytes. Such molecules may include, but are not limited to, antibodies, whole serum, tissue lysates, lectins, polymers, DNA/RNA molecules (e.g., extracted from patient fluids), oligonucleotides, T-cells, etc. Where probe molecules are DNA/RNA molecules, they may be extracted from fluids of an animal or plant. Fluids include, but are not limited to, blood, interstitial fluid, plasma, saliva, semen, etc. DNA/RNA molecules may also be detected by beads bearing a complimentary oligonucleotide sequence on their surface. Probe molecules may be charged or not charged.

Figure 3:
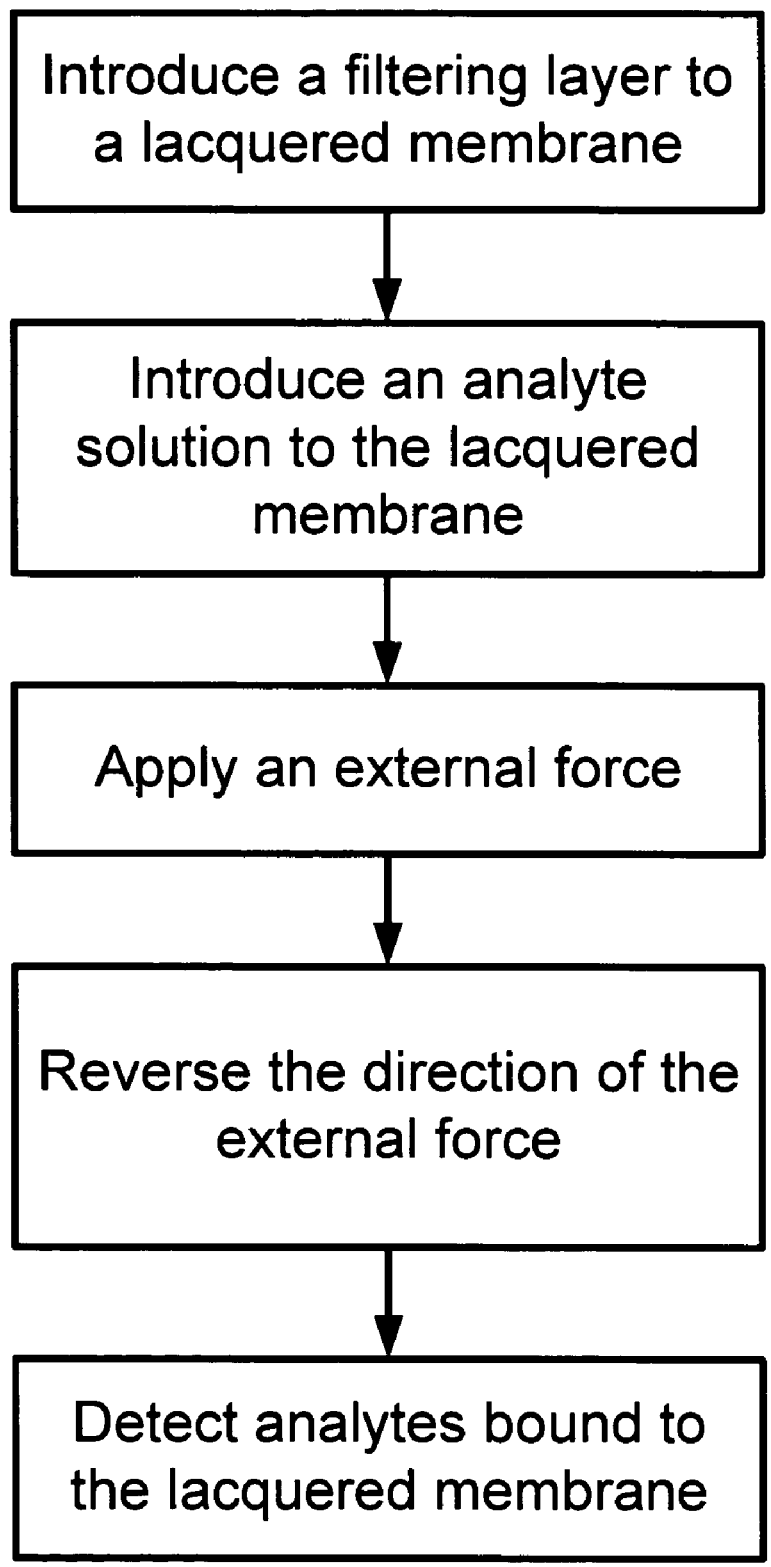
FIG. 3 shows a flow diagram of another embodiment of capturing analytes.

FIG. 3 shows another embodiment of capturing analytes. A filtering layer may be added. The filtering layer may comprise a plurality of filtering particles, such as Sephadex particles, Sepharose particles, Matrex Sellufine particles, their equivalents, etc. The filtering layer should come before the lacquered membrane in a way such that when the analyte solution is introduced, the analyte solution would pass though the filtering layer. As exemplified in FIG. 3, the filtering layer is situated above the lacquered membrane. When the analyte solution is poured into the vessel having the filtering layer and lacquered membrane, the filtering layer may separate analytes of interest from other compounds and content in the analyte solution. Guided by one or more external forces, analytes may pass through the filtering layer and head towards the lacquered membrane. Even though some of the content not of interest may pass through the filtering layer, this separation effect can result in more analytes binding to the probe molecules or lacquered membrane itself.

Another embodiment for capturing analytes includes alternating the external force direction. In addition to reversing the external force direction, the direction of the external force may be changed periodically. Doing so may aid in the lateral diffusion of analytes. Lateral diffusion may allow unbound analytes or weakly bound analytes to be reshuffled. In turn, if and when external force is again applied to the analyte solution, the remaining unbound analytes may be able to bind to either the lacquered membrane and/or probe molecules.

Some cross-linked polymers may not be capable of adsorbing or chemically binding probe molecules to the lacquered membrane. As one embodiment of enhancing improving adsorption or chemical binding, the lacquered membrane may be treated with an activation measure. Nonlimiting examples of activation measure include treatment in plasma discharge followed by treatment in a mixture of N-Hydroxysuccinimide (NHS) and water soluble carbodiimide (EDC), etc. Plasma treatment may result in a higher coating capacity. Treating the lacquered membrane with NHS/EDC may increase density of immobilized probes.

Figure 4:
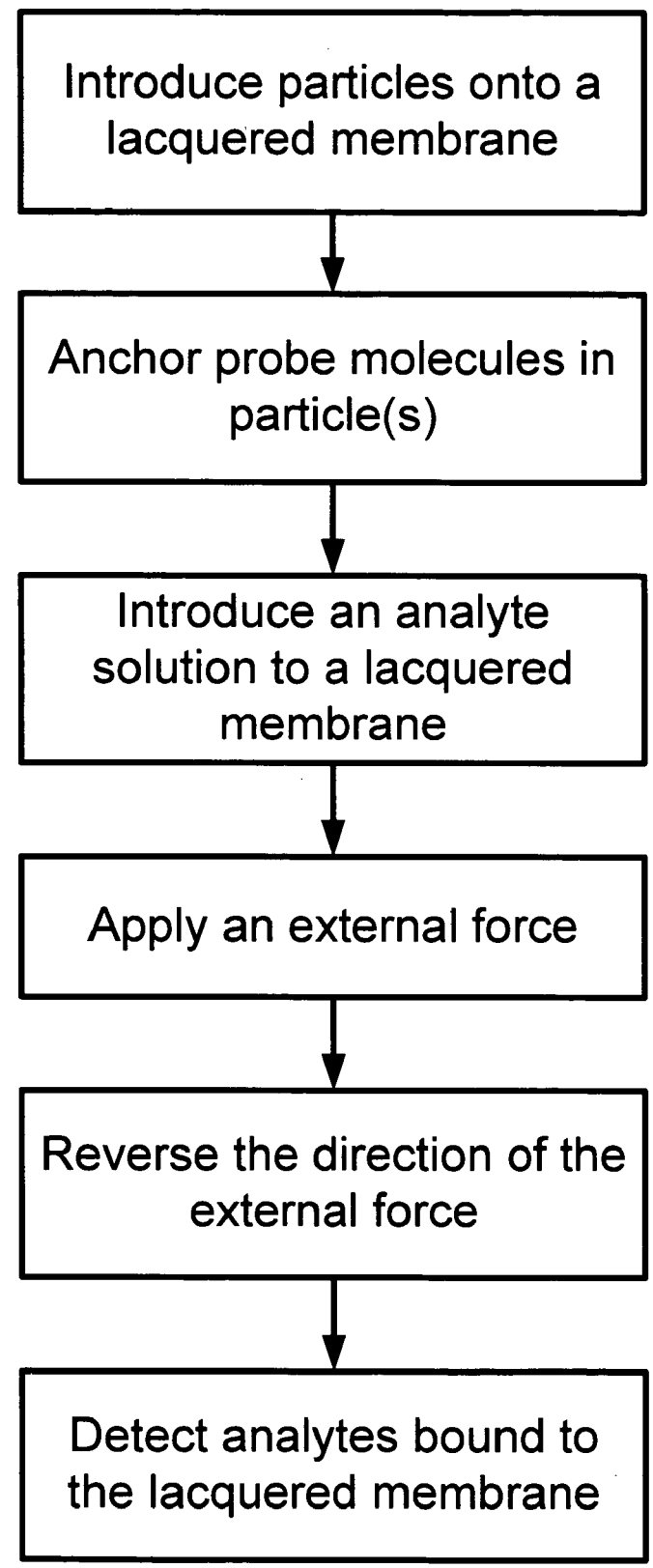
FIG. 4 shows a flow diagram of another embodiment of capturing analytes.

FIG. 4 shows another embodiment of capturing analytes. Particles may be used to link with analytes in an analyte solution. A nonlimiting example of these particles is functionalized beads, which may or may not be magnetized. In one embodiment, the combination may be directed using an external force to the lacquered membrane without probe molecules. One or more analytes bound to a particle may bind to the surface and thus detach from the particle. In another embodiment, the combination may be directed using an external force to the lacquered membrane with probe molecules bound to its surface. Hence, one more analytes bound to a particle may bind to the probe molecules. One bound, the analytes may detach from the particle. In both embodiments, the direction of the external force may be reversed to remove the particle. Moreover, both embodiments may incorporate a filtering layer to remove debris and nonanalytes.

Another method of capturing analytes includes collecting analytes onto an intermediary membrane. Collection may be achieved electrophoretically (e.g., via electrospray deposition). The intermediary membrane may be semi-transparent. The analytes may be deposited onto this intermediary membrane as an array. Once collected, these analytes may be transferred onto another membrane. Transferring may also be achieved in multiple ways. For example, the transfer can be made electrophoretically. Another way includes overlaying the intermediary membrane on top of another membrane (forming a sandwich), pressing the two membranes together to allow the deposited analytes to contact and collect on the other membrane, and gently removing the intermediary membrane by peeling. The transfer may create a microarray on the other membrane, which may be a lacquered membrane.

Figure 5:
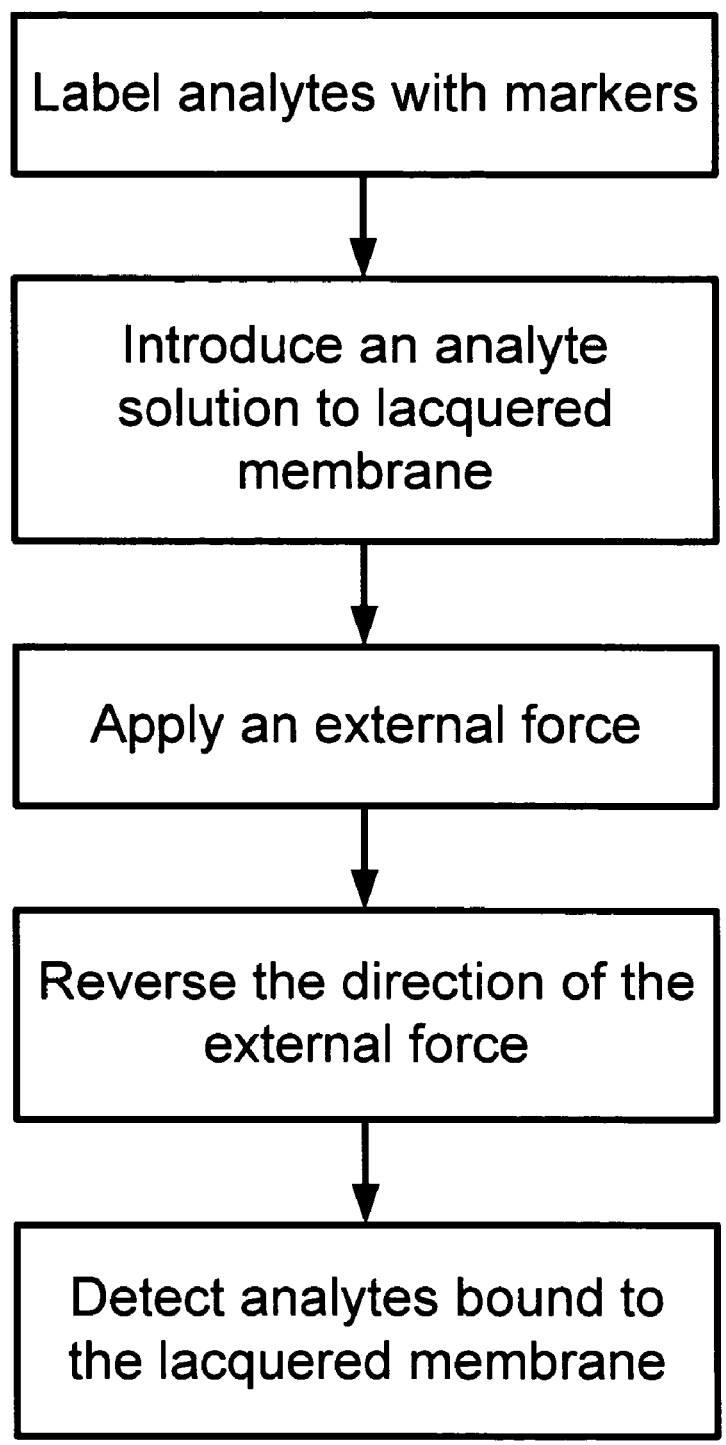
FIG. 5 shows a flow diagram of yet another embodiment of capturing analytes.

FIG. 5 shows yet another embodiment of capturing analytes. At times, analytes may be labeled with markers. These markers, sometimes referred to as labels, may be biospecific molecules. As in probe molecules, examples of markers include, but are not limited to, antibodies, lectins, polymers, DNA/RNA molecules, oligonucleotides, T cells, etc. Attachable to probe molecules, the markers may serve as binding components that bind with analytes. The markers aid in labeling the analytes prior to capturing by probe molecules. When markers are introduced to analytes (e.g., in an analyte solution), analytes may bind to and be captured by these markers. The same markers used to combine with the analytes may be used as probe molecules and be deposited on the lacquered membrane. When marker-analyte combination is introduced to the lacquered membrane with probe molecules, the combination may be captured by the probe molecules. Introduction may be accomplished using an external force. The filtering layer may also be used to filter debris. When the direction of the external force is reversed, the markers may detach and separate from the analytes, which may remain bound to the probe molecules. The direction of the external force may be periodically changed so as to allow lateral diffusion of these marker-analyte combinations over the lacquered membrane to occur.

Figure 6:
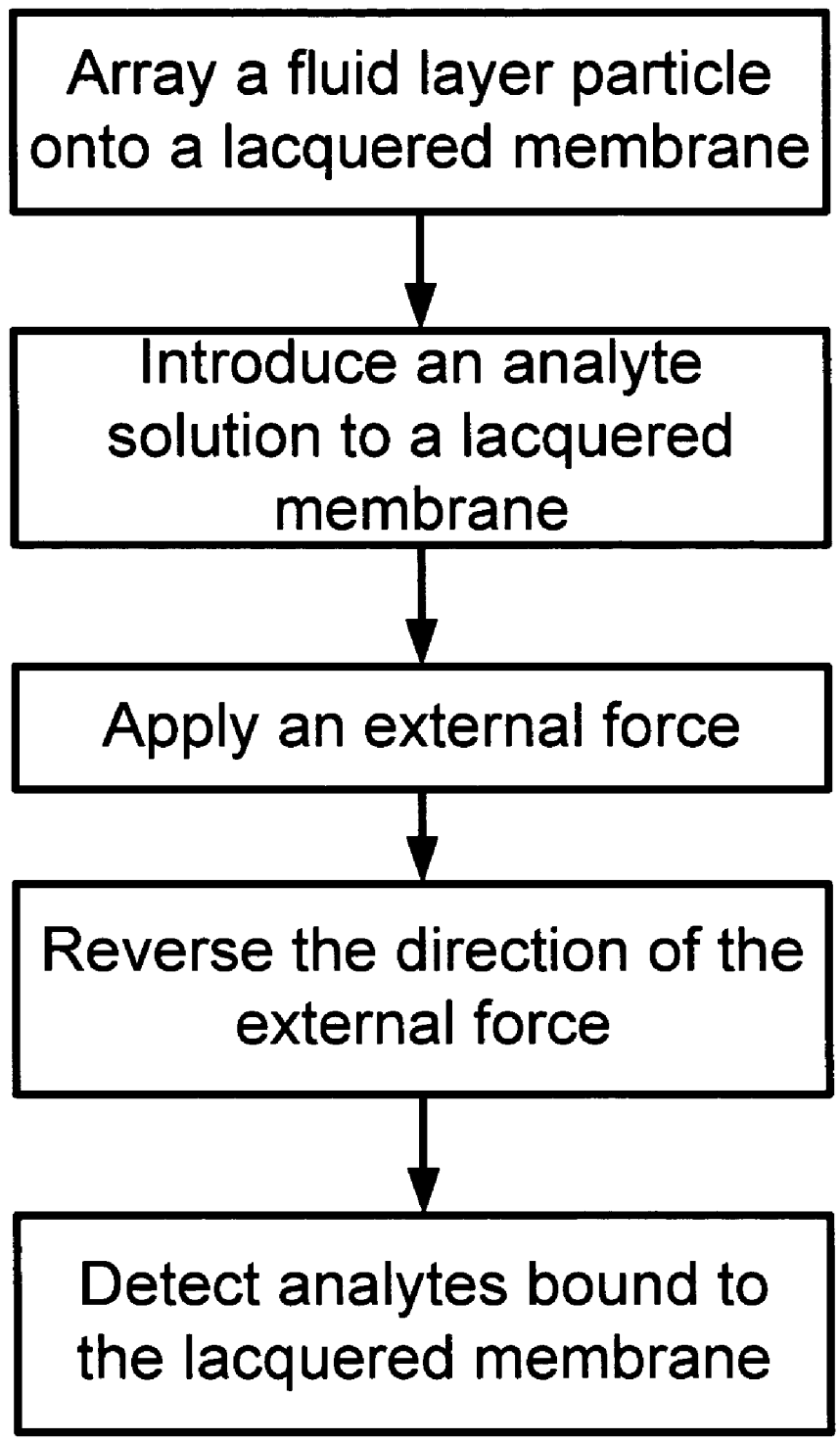
FIG. 6 shows a flow diagram of yet another method of capturing analytes.

FIG. 6 shows yet another method of capturing analytes. Probe molecules may be anchored to a lacquered membrane using particles. Particles, as described herein, include, but are not limited to, solids, fluids, natural and/or synthetic materials, organic, inorganic, etc. Where probe molecules are anchored in one or more fluid layers, the fluid layer may be a lipid mono-layer, a lipid bi-layer or an oil layer. This fluid layer may also be a liposome. The hydrophobic tails of the fluid layer may be bound to probe molecules. Probe molecules may be bound to an array surface by using long hydrophilic polymer chains as linkers.

Probe molecules (e.g., antibodies) may freely float in a lipid bi-layer. Their mobility enables formation of multiple parallel bonds with the antigenic determinants of the analytes, strongly tethering the latter to the spot. Separate antigens capable of forming only single bond with probe molecules (e.g., antibodies) tend to be unstable and quickly dissociate.

Where IgG molecules are included, the affinity of probe molecules to the lipid layer may be selected low enough to disable their interaction with separate IgG molecules. However, the combined affinity of several probe molecules to IgG molecules bound in parallel to an analyte may be high enough to keep the analyte bound for at least 30 sec.

Figure 7:
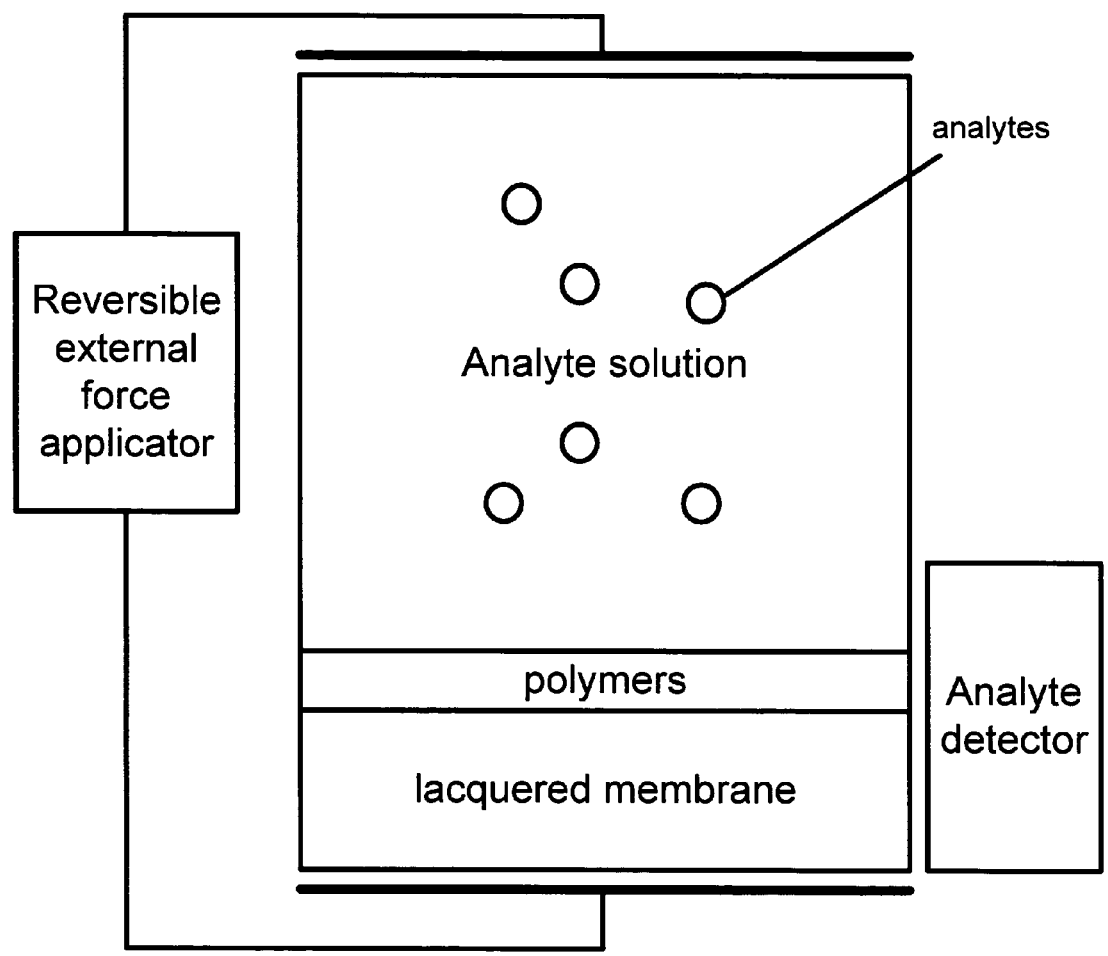
FIG. 7 shows a block diagram of an embodiment of an active assay system.

Each of these embodied methods and techniques may be practiced over an active assay system as depicted in FIG. 7. Such system may include a lacquered membrane, an analyte solution, a reversible external force applicator, and an analytes detector. As described above, the lacquered membrane may be any membrane, such as a dialysis membrane or a substrate membrane. It may be treated with cross-linked polymers, and it may be semi-permeable. The analyte solution should contain the analytes of interest. The reversible external force applicator can be any mechanism (e.g., a vessel, etc.) that is capable of applying one or more external forces to the analyte solution. Force application should result in moving the analytes toward the lacquered membrane. Additionally, the reversible external force applicator is capable of reversing the direction of the external force, allowing for the removal of unbound analytes or analytes that are weakly bound. Moreover, the reversible external force applicator may have the capability to periodically alternate the direction of the external force to allow lateral diffusion of analytes. With lateral diffusion occurring, more unbound analytes may be able to find and bind to binding sites.

Figure 8:
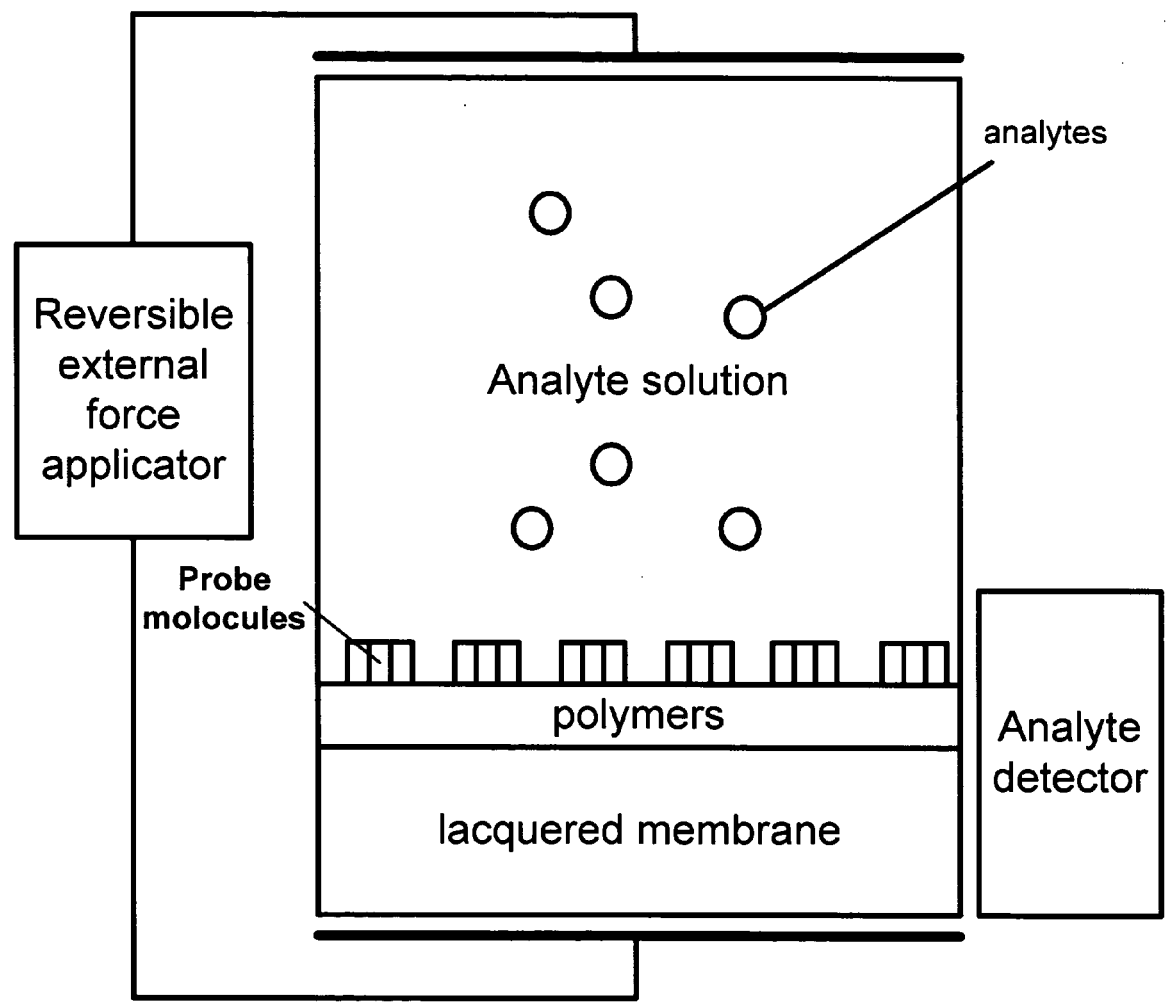
FIG. 8 shows a block diagram of another embodiment of an active assay system.
Figure 9:
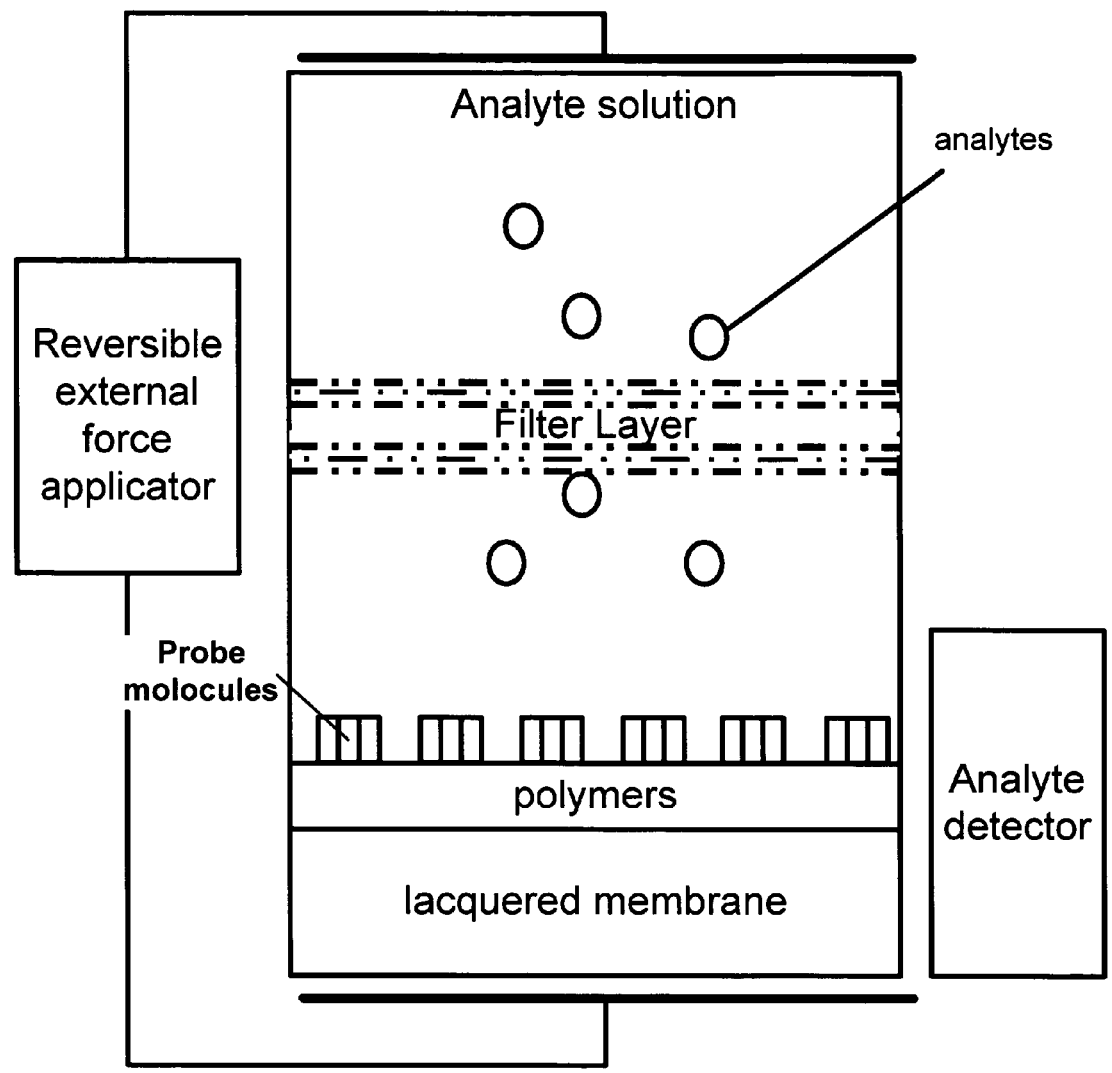
FIG. 9 shows a block diagram of another embodiment of an active assay system.

As another embodiment, the system may have probe molecules introduced to the lacquered membrane, as illustrated in FIG. 8. Additionally, a filtering layer may also be introduced to the system, as shown in FIG. 9.

Similarly, each of these methods and techniques may be practiced over an active assay apparatus. As in the system above, the apparatus may include a lacquered membrane, an analyte solution, a reversible external force applicator, and an analytes detector. As described above, the lacquered membrane may be any membrane, such as a dialysis membrane or a substrate membrane. It may be treated with cross-linked polymers, and it may be semi-permeable. The analyte solution should contain the analytes of interest. The reversible external force applicator can be any mechanism (e.g., a vessel, etc.) that is capable of applying one or more external forces to the analyte solution. Force application should result in moving the analytes toward the lacquered membrane. Additionally, the reversible external force applicator is capable of reversing the direction of the external force, allowing for the removal of unbound analytes or analytes that are weakly bound. Moreover, the reversible external force applicator may have the capability to periodically alternate the direction of the external force to allow lateral diffusion of analytes. With lateral diffusion occurring, more unbound analytes may be able to find and bind to binding sites.

As another embodiment, the apparatus may have probe molecules introduced to the lacquered membrane. Additionally, a filtering layer may also be introduced to the apparatus.

Lacquered Membrane

1. Introduction

When analytes are deposited on a substrate for detection via electron microscopy, AFM, etc., detection may prove to be difficult when the analyte concentration is low. One way to improve the assay is to apply an external force to an active collection of analytes. This application may direct the analytes to the substrate, which may or may not have probe molecules. For example, when an electric field is used to charge analytes and direct them onto a dialysis membrane for AFM imaging, the dialysis membrane should be conductive, non-penetrable for analytes and smooth enough to allow for the recognition and imaging of captured analytes.

The substrate may be a dialysis membrane, with semi-permeable/ultra-filtration properties, or any other semi-permeable membrane. Semi-permeability/ultra-filtration may serve as an advantage for allowing nonanalytes (e.g., salt ions, buffer ions, etc.) to penetrate through the membrane without being penetrable by analytes. For example, if an analyte is not penetrable below 100 angstroms below the surface of the membrane, the analyte may be considered as being nonpenetrable. By having nonanalytes penetrating through the membrane, the concentration in the analyte solution may be reduced. Thus, detection of analytes may become more accurate.

A semi-permeable membrane can be any membrane known in the art that is capable of binding an analyte and/or a probe molecule. Examples include those produced by Spectrum Laboratories, Inc. While one dialysis membrane may be used, the scope of this disclosure is not limited to the use of only one dialysis membrane. In fact, more than one may be used simultaneously. Any one of these multiple dialysis membranes may immobilize and array probe molecules.

A dialysis membrane may be prepared from a regenerated cellulose (such as those produced by Sigma-Aldrich, Spectrum Laboratories, etc.). Typically, membranes prepared from regenerated cellulose can be optically transparent and mechanically strong. The surfaces may be activated with polymers, such as cross-linked polymers (which may be functionalized with proteins), nucleic acids, polysaccharides and other probe molecules, to facilitate the adsorption of analytes.

Figure 10:
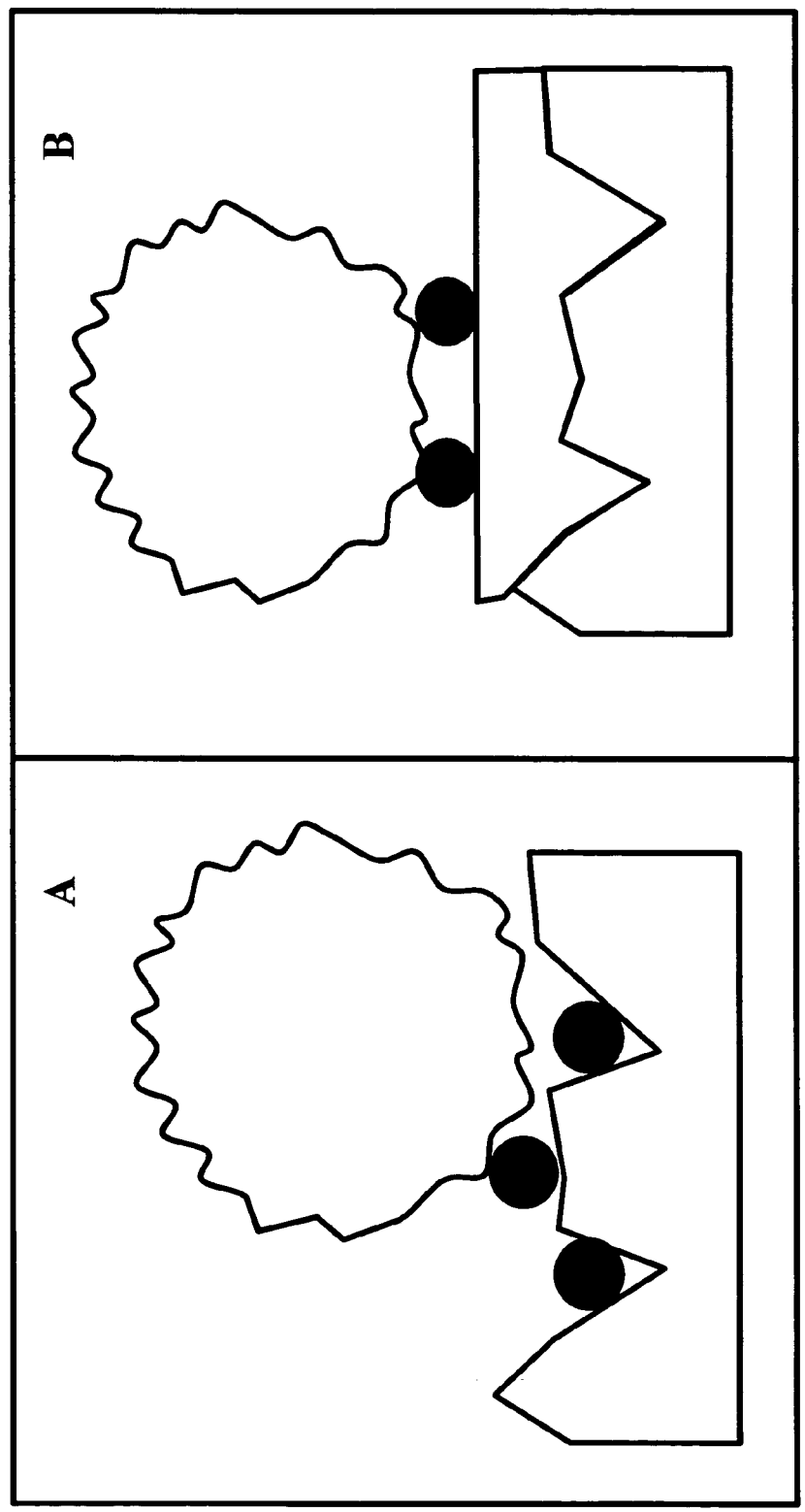
FIG. 10 shows bead detection of a pathogen captured on a rough (A) and smooth (B) membrane surfaces.

While existing dialysis membranes can satisfy the first two conditions, they are often not smooth enough to allow imaging of small analytes, such as viruses, phages, protein toxins, antibody molecules, etc. As seen in FIG. 10, part of the captured pathogens may be "lost" in surface defects and thus become unobservable.

2. Manufacturing a Lacquered Membrane with a Smooth Surface

Generally, commercially available dialysis membranes tend to have a rough surface that may be due to the roughness of an extruder surface used in their fabrication. The rough surface may also be due to nodule formation upon aggregation of the membrane material during pore formation.

Images of multiple commercial membranes were obtained by AFM and analyzed. As shown in the FIG. 11, roughness measured in an area of 0.5 $\mu m^2$ can vary between 4 and 8 nm among the commercial membranes tested. One particular feature observed in all the surfaces is arrays of deep cavities. These deep cavities can potentially "hide" bound analytes from observation by probing magnetic beads, by the AFM tip and even by secondary antibody molecules.

a. Prelacquering Dialysis Membrane

To smooth the surface roughness without affecting the dialysis membrane's ultra-filtration properties, a couple of techniques may be used. Generally, the techniques involve applying polymers (e.g., cross-linked polymers, natural polymers (with or without synthetic properties), synthetic polymers, etc.) to the surface of the dialysis membrane. However, because layers of polymers tend to peel off the surface when directly applied, surface adhesion should be enhanced. As one embodiment, the dialysis membrane may be treated with plasma discharge to enhance adhesion of glues and/or coating by introducing a variety of functional groups.

Prior to plasma treatment, plasma effects on the surface roughness may be tested. One way of testing this effectiveness is using the following exemplified procedure.

To enable simultaneous measurements of etching depth and changes in the surface roughness, part of the surface may be protected with dry sucrose prior to plasma treatment. Sucrose may be electrospray deposited from a 2% water solution through a polystyrene or nylon mesh mask on a dialysis membrane surface as an array of dry spots, where each spot may be approximately 10 µm in diameter and spaced apart by 50 µm. After deposition, the membrane may be briefly exposed to damp air to produce microdroplets of sucrose solution, which may then be dried in a stream of warm air forming dry sucrose caps of about 1.5-2 µm thick. After exposure to plasma discharge, the membrane may be placed in water for 3-5 min to dissolve the residual sucrose layer and expose protected spots. Small disks (approximately 5-7 mm in diameter) may be punched from the membrane and glued to a microscope slide using 5% poly(vinylpyrrolidone) (PVP). The surface of protected spots may be used as a reference in measurements of ablation depth under AFM.

Ablation depth may be used as a measure of plasma treatment in evaluating the effect in terms independent of the specific geometry of the plasma reactor, power distribution inside the reactor and other details. To measure the ablation depth, an array of protective dry sucrose spots may be fabricated on the membrane surface as described above. After treatment in plasma and washing sucrose away, two independent parameters may be determined in different places on the membrane: depth of ablation in plasma (measured as a height of a step at the boundary between protected and unprotected areas) and the average roughness of the plasma-treated surface. Generally, the level of roughness increased as the area measured was increased. Thus, roughness of the dialysis membrane treated for 20 sec in plasma slowly increased from 3 to 8 nm at S=0.5 µm² to 15-20 nm at S=250 µm². Surface roughness may be characterized by measuring the rms roughness within a 0.7 µm square, which may be close to the size of analytes (e.g., fd bacteriophages).

Figure 12:
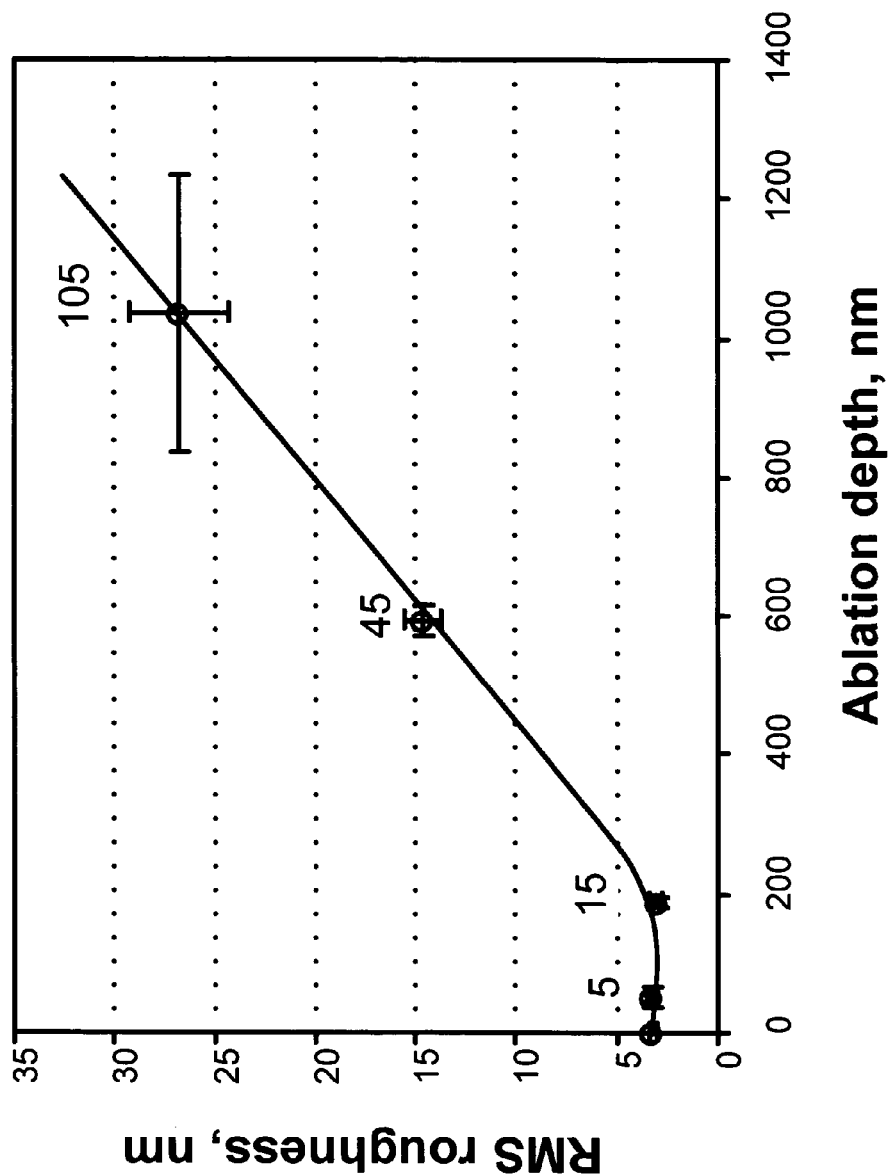
FIG. 12 shows rms roughness of a surface of a dialysis membrane as a function of ablation depth resulting from plasma treatment.

As shown in FIG. 12, no notable changes in the surface roughness are observable after a short-term (e.g., 10-15 sec) exposure to plasma, when etching depth does not exceed 200 nm. Deeper ablation may be accompanied by an increase in the surface roughness, which may increase by approximately 30 nm/1 µm of ablation. Hence, a short-term exposure to plasma (e.g., 15-20 sec) may be used to activate surface of the membrane before "lacquering".

b. Lacquering Dialysis Membrane

Having treated the surface of the dialysis membrane with plasma, the ability of polymers to stay on the surface once introduced increases. In essence, one technique of smoothing the surface may be seen as in FIG. 13. A polymer solution, having polymers such as the cross-linked polymers as embodied above, may be applied to the surface of the dialysis membrane attached to a ring. The solution is facing a Petri dish. Typically, as the polymer solution is slowly dried through the dialysis membrane, a thin and smooth polymer layer is allowed to form at the air/solution interface. This additional layer may have a size of, as non-limiting examples, at least 1 nm, 5 nm, 10 nm, 25 nm, 50 nm, 100 nm, 250 nm, 500 nm or even 1 µm.

Figure 11:
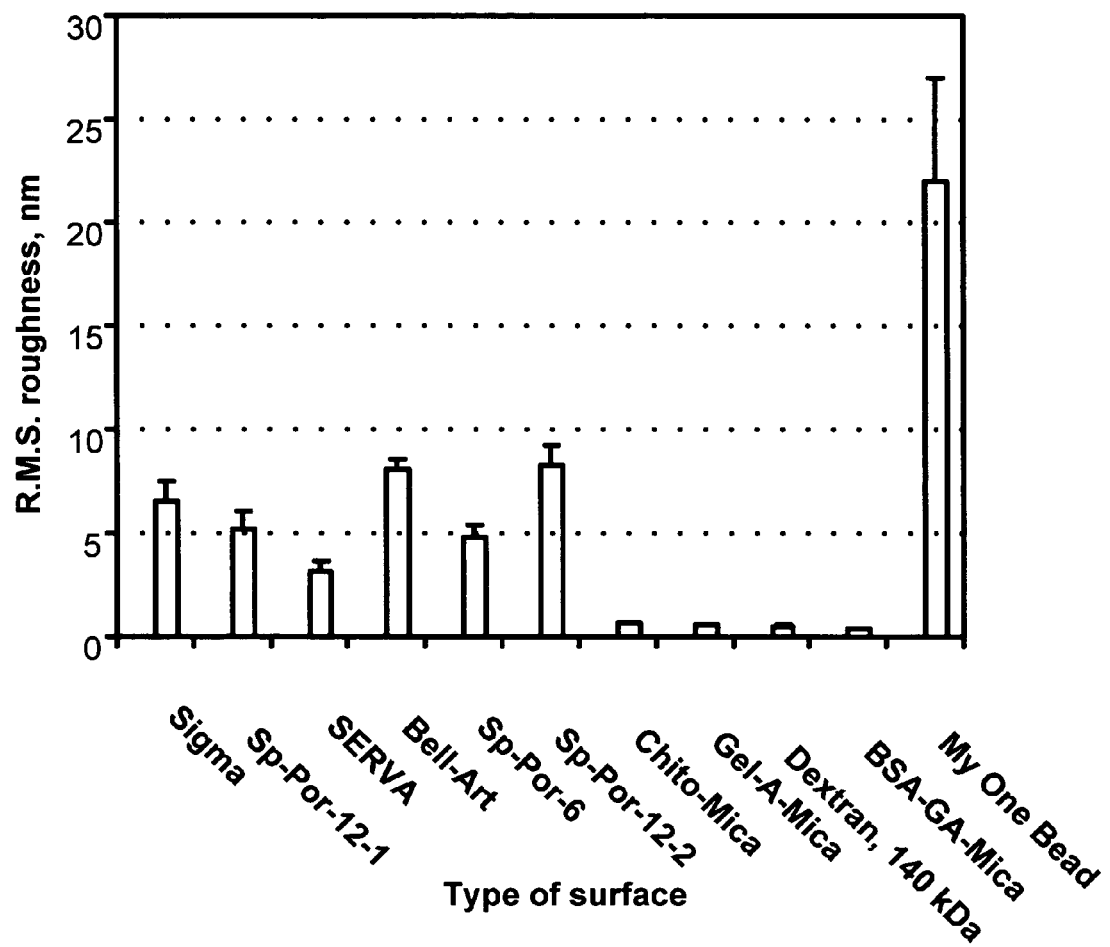
FIG. 11 shows rms roughness of surfaces of dialysis membranes obtained from different vendors as well as roughness of modified surfaces.

Various cross-linked polymers were tested. Examples include, but are not limited to, gelatin A, gelatin B, chitosan, dextrans and globular proteins. Among those tested, coating the substrate with globular protein BSA resulted in the smoothest surface. A BSA molecule has an average diameter of about 5 nm. As depicted in FIG. 11, the root mean square (rms) for roughness was about 0.3-0.4 nm. If smaller rms roughness of the BSA surface exists, it is possible that there may be partial unfolding of BSA globules on the surface. If AFM is performed, then it is possible to have a smaller rms because of a relatively large radius on the AFM curvature tip (i.e., approximately 10 nm), which may overlook small cavities between BSA globules.

Figure 13:
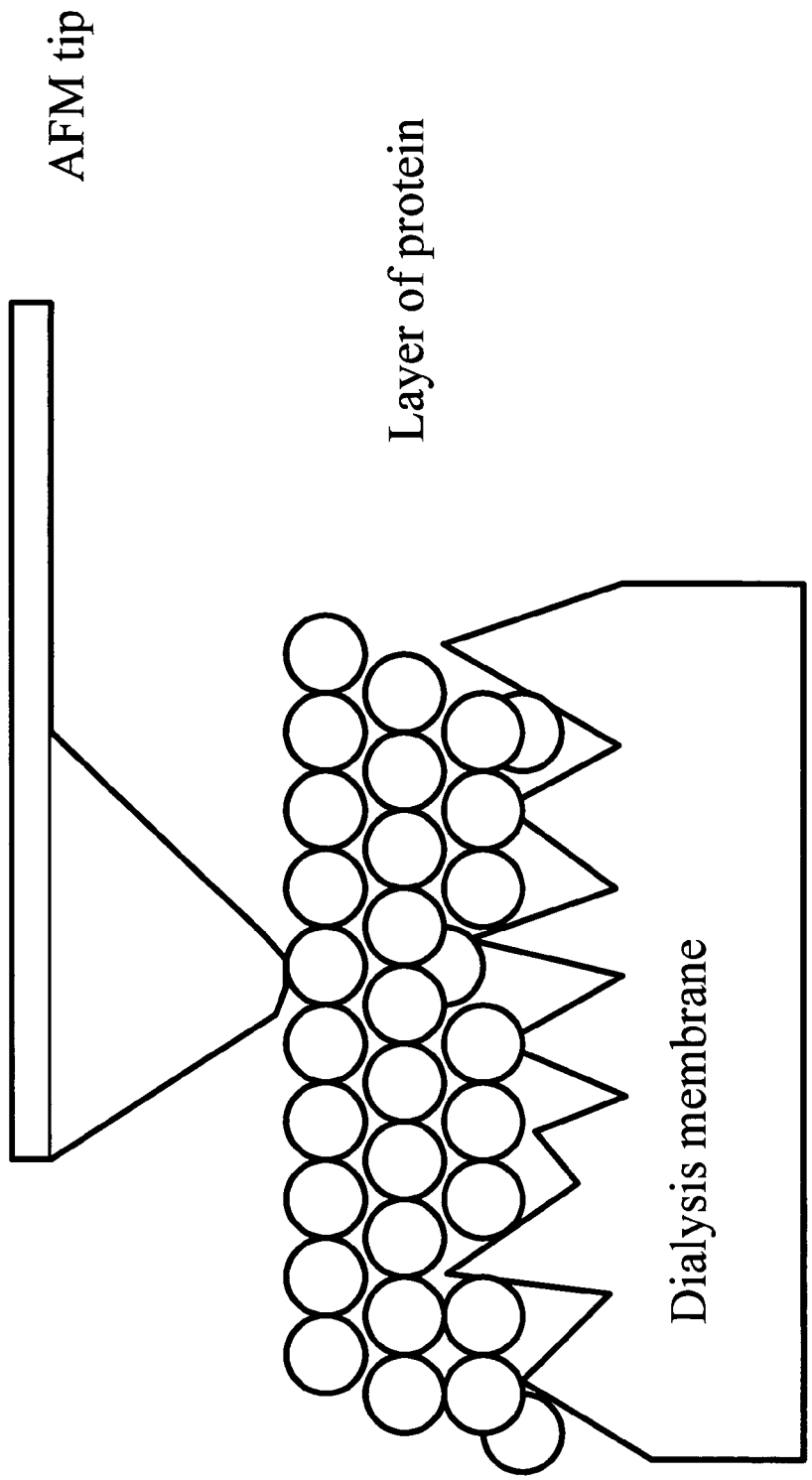
FIG. 13 shows lacquering of the membrane surface with a layer of globular proteins, where the upper layer of protein molecules is smoothed by surface tension at the air-solution boundary.

By filling in irregularities on the surface of the membrane, the layer of cross-linked polymers may produce a smooth surface, as illustrated in FIG. 13. Smoothing the layer may be achieved by having the upper layer of the cross-linked polymers flattened by surface tension.

In another technique, the dialysis membrane may be coated with the polymer sandwiched between the membrane and a mica layer. A smooth layer surface generally is formed at the solution/mica interface when water evaporates through the membrane.

In certain situations, the lacquered membrane may need to be activated to facilitate the adsorption and/or the covalent bonding of analytes and/or probe molecules. Activation may be achieved by treating the cross-linked membrane with an activation mixture. An example of an activation mixture is NHS/EDC.

In another embodiment, the surface of the dialysis membrane was lacquered with cross-linked dextran. It was found that oxidized dextran (e.g., 40 kDa, 40% oxidation) mixed with a bi-functional cross-linker (e.g., adipic acid dihydrazide (AAD)) may produce a highly transparent and strong film upon drying. Once applied on a dialysis membrane, such film may not require further activation for protein binding since a large number of free aldehyde groups may still remain on the cross-linked dextran molecules. If probe molecules, such as antibodies, were linked to long dextran chains, they may be able to freely move, access and accommodate antigenic determinants of the captured analytes. Hence, one advantage of cross-linked dextrans is the simplicity of the coating procedure.

c. Lacquered Membrane Cross-Linked with BSA

1. Example 1

Figure 14:
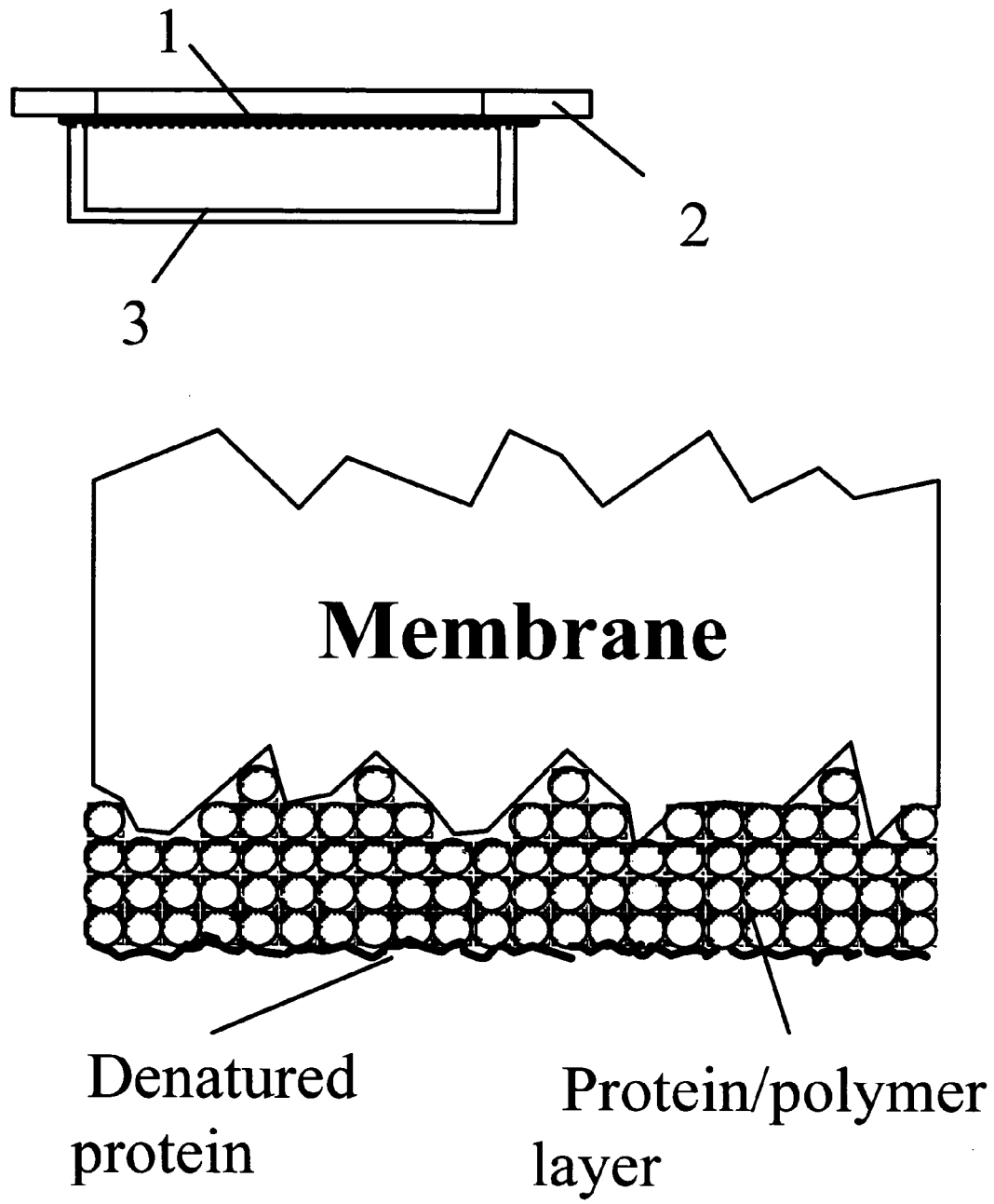
FIG. 14 shows an embodiment of depositing of a layer of cross-linked globular BSA on an activated dialysis membrane.

Using the technique shown in FIG. 14, a layer of cross-linked globular BSA may be deposited onto the surface of an activated dialysis membrane.

The dialysis membrane (1) was first placed in distilled water for several minutes. A plastic ring (2), with an inner diameter of 60 mm and an outer diameter of 90 mm fabricated from a 3 mm thick polycarbonate plate, was treated in radio frequency (Rf) plasma discharge for 20 sec. and placed in water for 1-2 min. Water was removed from the ring, and a layer of a cyanoacrylate glue was applied to one side. Wet Whatman paper was placed on a plastic sheet. The dialysis membrane was placed on the paper face down, and excess water was removed from the membrane by a photographic roller. The ring was then placed on the wet dialysis membrane with the glue side contacting the membrane. Together, they were pressed with clamps for about 30-60 sec. The ring with the glued wet membrane was then removed from the paper and placed in a vertical holder for 2-3 hours to dry and to evaporate the cyanoacrylate monomer. All the operations with the cyanoacrylate glue were performed in a fume hood.

After drying, the dialysis membrane shrank and formed a perfectly flat surface suitable for arraying. The dry membrane was treated in plasma discharge for 20 sec to activate surface groups. After treatment, it was then brought in contact with a freshly prepared solution of 0.05 M NHS and 0.2 M of EDC in water for 7 min to activate the carboxyl groups formed by the plasma on the membrane surface. The ring with the membrane was washed in 0.5 L of water with stirring for 5 min. Excess water was removed by brief centrifugation, such as at 13,400 r.p.m. for 10 min. BSA solution (0.1-0.2 mL of 1-5% solution) was applied and evenly distributed over the activated surface. The ring was placed onto a small (60 mm in diameter) Petri dish (3). The BSA coated membrane was placed face down into the closed space of the Petri dish without contacting the dish surface, so that protein layer was allowed to dry through the membrane only. Protected from capturing dust particles upon drying, the protein layer was slowly dried through the dialysis membrane in a fume hood for approximately 15-20 mins. Drying was performed in a mild stream of air created by a hood. Drying through the dialysis membrane and protection of the BSA layer from dust improved the smoothness of the surface. After drying was completed, the ring was placed into a closed 2 L chamber containing glutaraldehyde (GA) vapor (50 µL of 25% GA solution placed at the bottom of the chamber) for 30 min.

The surface of cross-linked BSA was highly hydrophobic, presumably due to exposure of the hydrophobic groups of the denatured protein at the air/water interface. The surface remained hydrophobic even after prolonged storage (i.e., 2-3 weeks) under blocking solution (20 mM TRIS/HCl, pH=7.5, 0.15 M NaCl, 0.1% Tween-20, 1% BSA).

2. Example 2

Figure 15:
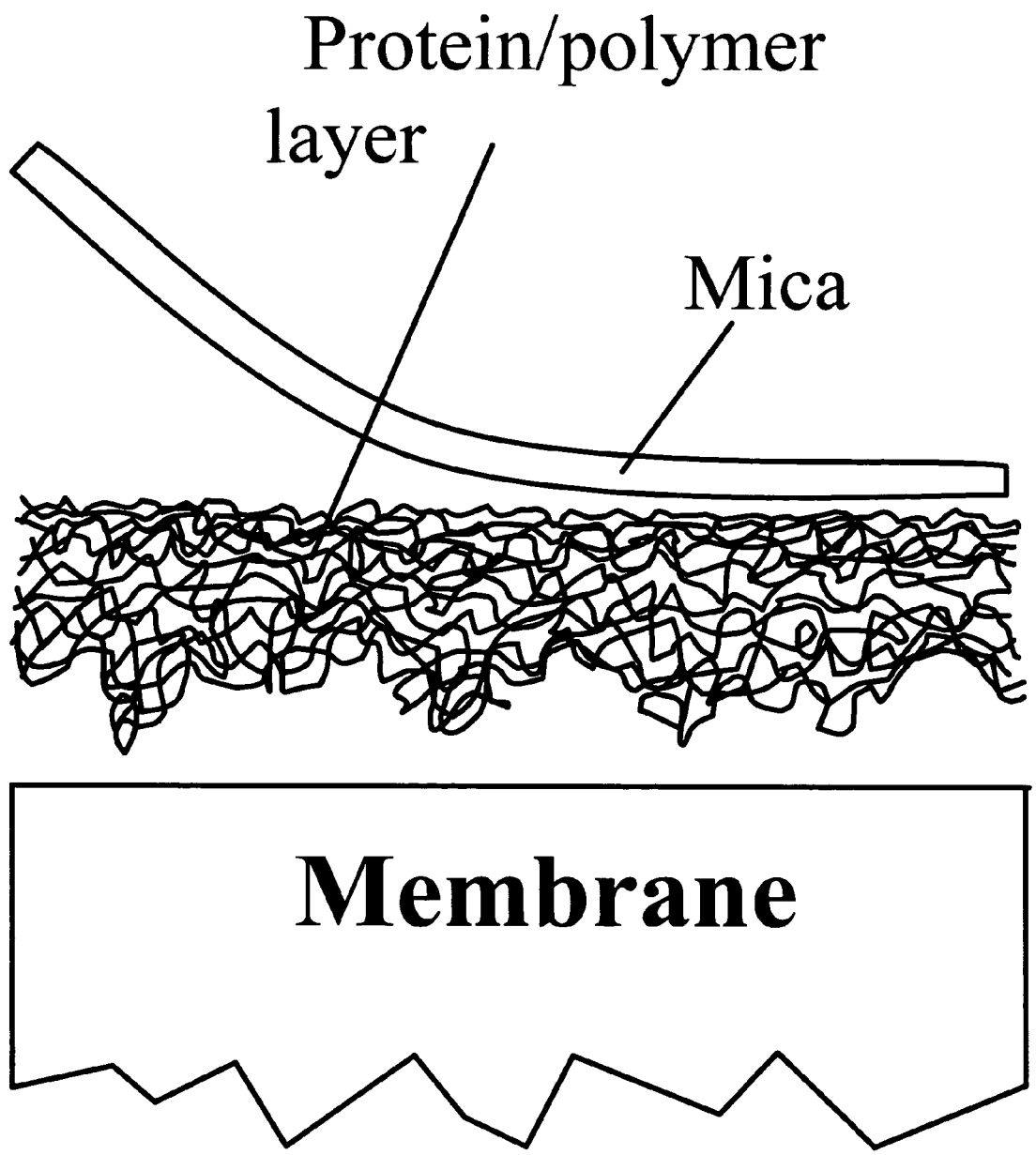
FIG. 15 shows another embodiment of depositing of a layer of cross-linked linear or branched polymer on an activated dialysis membrane.

A layer of cross-linked linear or branched polymer may be deposited onto the surface of an activated dialysis membrane using the technique shown in FIG. 15.

Here, the dialysis membrane was prepared as in Example 1. However, after the rinsing and spinning was completed, the membrane was cut off the ring and placed face down onto a layer of BSA solution (0.1-1%). This BSA solution was placed on a surface of mica that was glued (e.g., using epoxy glue) to a glass plate. The membrane was covered with Whatman paper and pressed with the roller to distribute the solution between mica and membrane surfaces. The Whatman paper was then removed. Afterwards, the membrane and BSA solution were allowed to dry in a hood.

As in the first "lacquering" procedure, drying occurred through the dialysis membrane. Dry dialysis membrane was then carefully peeled off the mica, and the layer was cross-linked in GA vapor as described above. Though it was possible to peel the membrane off the freshly cleaved mica, such detachment became much easier if hydrophobic mica was used. Hydrophobic mica was prepared by a 20 sec treatment in the plasma discharge followed by reaction with a dichlorodimethylsilane (DDS) vapor in nitrogen for 7 min and baking the DDS layer for 1 hour at 100° C.

d. Lacquered Membrane Cross-Linked with Gelatin

Dialysis membrane was coated with gelatin using the same procedures as described for BSA.

e. Lacquered Membrane Cross-Linked with Chitosan

Dialysis membrane was coated with gelatin using the same procedures as described for BSA.

f. Lacquered Membrane Cross-Linked with Oxidized Dextran

1. Oxiation of Dextran

The following procedure demonstrates one embodiment of how dextran can be oxidized.

Periodic acid monohydrate (0.55 g) was dissolved in 10 mL of water. The pH was adjusted to 5.5 with NaOH. A 0.5 g amount of solid dextran was added to the solution, and the mixture was kept in the dark at room temperature for 2 hours. The oxidized dextran was dialyzed in the dark for 48 hours at 4° C. until the conductivity reached 25-35 µS/cm. The concentration of the oxidized dextran was determined gravimetrically: a residue obtained after evaporation of 50 µL of the stock solution was weighted on a Cahn microbalance.

The percentage of oxidized glycoside residues were determined by hydroxylamine titration. A 0.1 mL volume of 3-5% dextran solution and 0.3 mL of 0.4 M $NH_2OH/HCl$ were added to 2.6 m/L of water. The reaction was allowed to proceed at 40° C. for 2 hours, and the protons liberated were titrated with a 0.1 M NaOH solution under nitrogen.

2. Example

In this example, it was found that if dried in the presence of AAD as a cross-linker, the oxidized dextran may form a strong, transparent, insoluble film when the AAD to dextran ratio (W/W) was 1:10.

A dry dialysis membrane glued to a plastic ring as described above was treated in RF plasma for 20 sec. A solution containing 1% oxidized dextran (40 kDa, 40-50% oxidation of glucoside residues) and 0.1% AAD was prepared. Of this solution, 0.1-0.2 mL was distributed over approximate 10 cm² of the membrane surface. The dextran layer was dried through the membrane support as described for the BSA coating to avoid deposition of dust particles on the coating. To ensure complete cross-linking, the membrane was kept at 85% humidity for 1 hour in a humid chamber containing a saturated $Na_2SO_4$ solution at its bottom.

g. Coating BSA/GA-Lacquered or Dextran-Lacquered Membrane with PEI

Either lacquered membrane coated with BSA/GA or dextran may be placed in a freshly prepared 1% solution of poly(ethyleneimine) solution (PEI) with a pH of 7.5 for 20 min. Afterwards, the lacquered membrane may be rinsed with water, separated from the plastic rind and kept in water until used. Usage should be within 2-3 hours after placement in water.

h. Comparison of Dialysis Membrane Treated with Cross-Linked Polymers

Figure 16:
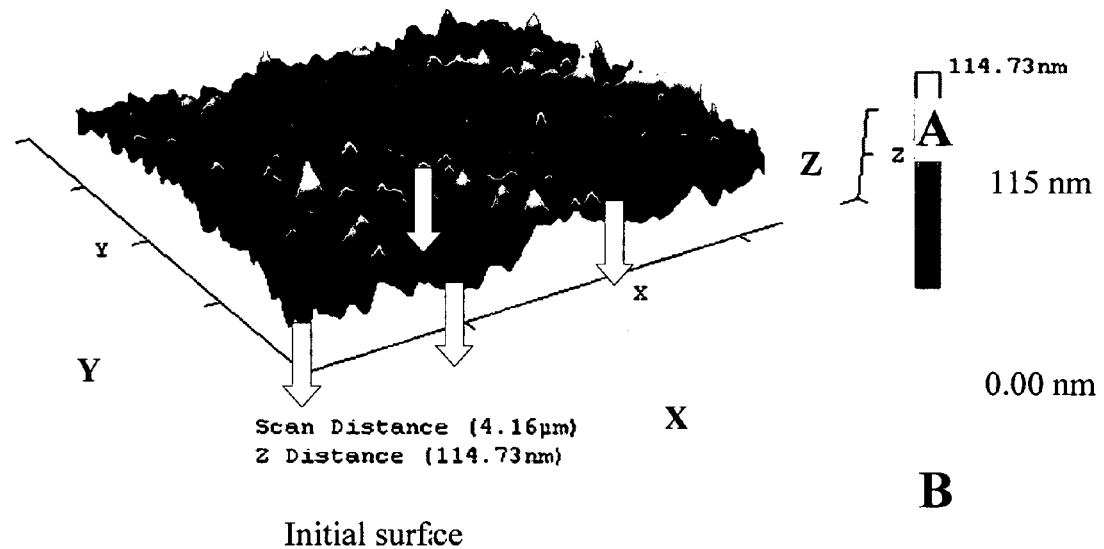
FIG. 16 shows AFM images of the initial surface of a dialysis membrane (A) and that after coating with BSA/GA (B).
Figure 16:
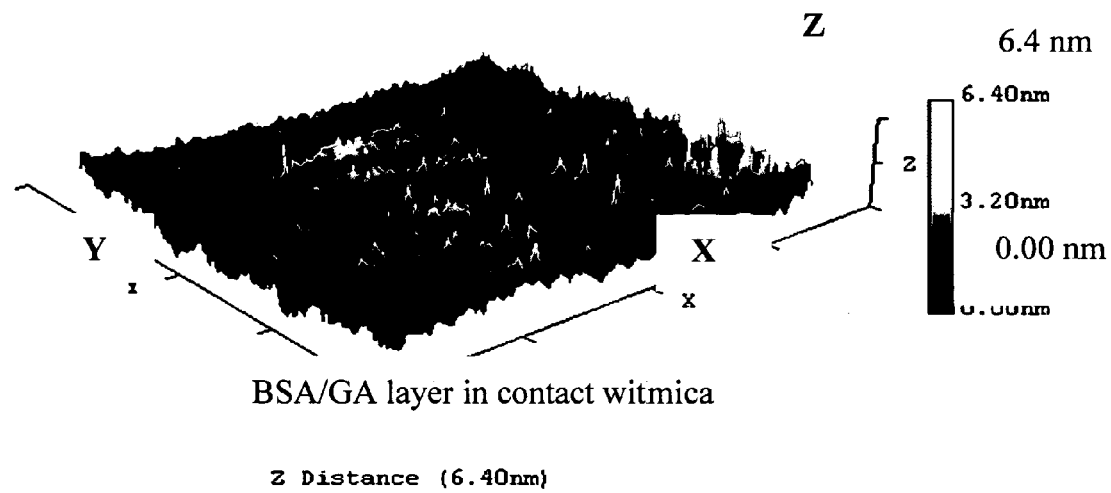

Various commercial membranes tested displayed surface rms roughness between 3 and 8 nm, when measured within S=0.5±0.05 µm. One characteristic feature of all the surfaces was an array of holes up to 60 nm deep. Such holes may be seen in FIG. 16A. The holes remain visible on the coated membranes, although their depth may be reduced to 10-20 nm on BSA/GA and dextran-coated surfaces (see FIGS. 17 and 18). These relief features may propagate through a relatively thick coating. The theoretical thickness of the polymer layers obtained from 10 µL of a 1% polymer solution dried over 1 cm² of the membrane surface is approximately 1 µm. However, the thickness may exceed the roughness of the dialysis membrane itself. One possible explanation for the persistence of large relief feature involves slower dynamics of smoothing for larger wrinkles on a wet polymer film due to a lower pressure difference operating under such large scale features. In this respect, drying the polymer solution through the dialysis membrane may add another benefit in addition to protection of the polymer surface from dust. Namely, it may slow down drying to give more time for smoothing.

As shown in Table 1, coating the surface of the dialysis membrane with dried cross-linked BSA, gelatin and oxidized dextran may reduce the surface roughness to 0.8-1.6 nm. A smoother surface may be obtained when the polymer layer is dried in contact with mica. With mica, rms roughness as low as 0.4-0.6 nm may be achieved. Part of the latter value may originate from noise since similar roughness measurements for freshly cleaved mica surface gave 0.17±0.02 nm, which may be approximately 2-fold larger than the roughness reported for mica.

While BSA molecules may have an average size of 5 nm, coating the dialysis membrane with BSA molecules may still produce a surface having an rms roughness as low as 0.5 nm. One explanation is that BSA molecules in the upper layer are expected to unfold completely or partially, as all proteins do at the water/air interface. Another explanation is that when dried, BSA molecules may be deformed by capillary forces and thus may substantially change their conformation so that spaces between the adjacent molecules become minimized. These changes may be partially fixed with glutaraldehyde. Additionally, very narrow holes between BSA molecules may be beyond the resolution of an AFM scanning tip with a radius of approximately 10 nm. Similar explanations can also be made for other polymer coatings (e.g., oxidized dextran, etc.) as well.

As shown in Table 2, the roughness of the dextran layer appears to be similar to that of the BSA/GA layer. The cross-linked dextran layer may also provide a surface smooth enough for most cases in analyte capturing. However, a layer of oxidized cross-linked dextran has several advantages over BSA/GA. For example, the oxidized cross-linked dextran layer may provide a higher surface density of the reactive carbonyl groups. Probe molecules, such as antibodies, may be bound to the dextran layer via longer spacers/linkers (e.g., dextran fee chains, loops and trains). The dextran layer may have less immobilized charges at a neutral pH (e.g., weak anion exchanger), which may reduce membrane polarization in electrophoretic processes. Additionally, unlike BSA/GA, the dextran layer is non-fluorescent. Moreover, using dextran can be simpler (e.g., performing 2 operations as opposed to 5 as in BSA/GA). Furthermore, using dextran can provide the presence of active aldehyde groups. These groups may eliminate the need to any additional surface activation.

TABLE 1

Roughness of Dialysis Membranes Coated with Different Cross-linked Polymers in Contact with Air and in Contact with Mica

| Type of Coating | Dried in Contact with Air, RMS Roughness, nm | Dried in Contact with Mica, RMS Roughness, nm |
|---|---|---|
| BSA/GA | 0.8 ± 0.06 | 0.42 ± 0.05 |
| Gelatin-A/GA | 1.6 ± 0.03 | 0.54 ± 0.05 |
| Chitosan | | 0.64 ± 0.08 |
| Oxidized Dextran/AAD | 1.3 ± 0.3 | 0.72 ± 0.03 |
| Oxidized Dextran/ AAD + PEI | 0.75 ± 0.1 | |

TABLE 2

Comparison of BSA/GA, Dextran-AAD and Bare Dialysis Membrane Surfaces

| Characteristics | BSA/GA layer | Oxidized Dextran-AAD layer | Bare dialysis membrane |
|---|---|---|---|
| Surface roughness in 0.5 µm² area, nm | 0.8 ± 0.06 (dried in contact with air) | 1.3 ± 0.3 (dried in contact with air) | 6.5 ± 1.0 |
| Activity in direct ELISA (OD at 405 nm) | 0.03 ± 0.01 | 0.41 ± 0.12 | — |
| Ion-exchange properties | Strong anion - exchanger at pH > 4.8 | Weak anion exchanger | Weak anion exchanger |
| Chemical groups | Carbonyl | Carbonyl | Non-reactive hydroxyl |
| Density of reactive groups | Low (see ELISA activity) | High | 0 |
| Spacer/Linker | None | Up to ~10 nm for 40 kDa dextran | |

Testing the applicability of the lacquered membrane as a substrate, PVP nanofibers electospun from a 5% solution of this polymer in water were imaged using AFM. Electrospinning may produce a spectra of fibers with diameters ranging from those of single polymer chains (e.g., ~0.3 nm in height) to hundreds of nanometers. Results of imaging showed that the smoothness of the lacquered membrane coated with oxidized dextran permitted imaging of PVP fibers with an average height of 1 nm.

3. Measurements of Membrane Conductivity

Since the lacquered membranes were prepared for electrophoretically capturing analytes, it may be necessary to determine if coating changed the electric (ionic) conductivity of the membranes.

As one way of how this determination may be made, the following embodiment may be performed.

Membrane disks may be cut with a puncher. The diameter of these disks may be 6.6 mm. The membranes were soaked in 10 mM MES buffer having a pH of 6.0. After equilibration in a buffer solution, a stack of disks was placed between two transparent conductive glasses coated with indium tin oxide (ITO). Buffer squeezed from the stack was measured as a function of the number of membranes in the stack using a standard ac conductivity meter. The average membrane resistance was estimated by dividing the total resistance by the number of membranes in the stack.

The resistance of the membrane may be approximately 3 times higher than the resistance of a buffer layer of equivalent size. Coating may increase membrane resistance only slightly. While 1 cm² of the dialysis membrane (having a thickness of 85 µm) may have a resistance R=96±14Ω, resistance of the same membrane after coating with a layer of either BSA/GA or dextran was 118±15Ω and 100±14Ω, respectively. At a typical current of 4 mA/cm² used in capturing analytes, the voltage difference across the membrane is generally only 0.4V and the heat release corresponds to generally 1.6 mW/cm². Thus, neither the membrane itself nor the BSA/GA or dextran coatings on the membrane interfere with the electrophoretic process.

4. Capturing Analytes on Lacquered Membrane a. Lacquered Membrane Surface

To exemplify the ability of lacquered membranes to capture analytes for imaging, fd bacteriophages (fd phage) were used. Fd phage is a filamentous virus 0.7-0.8 µm long and 6 nm in diameter. An initial dialysis membrane (e.g., a semipermeable membrane that has not been treated with cross-linked polymers) with roughness of 4-8 nm may not allow for imaging such small object. However, when the dialysis membrane was coated with BSA or dextran, fd phages may be observed.

One way to capture analytes onto the surface is electrocapturing. This process generally involves adding a charged polymer, such as PEI, to the lacquered membrane. When oppositely charged analytes are introduced to the charged lacquered membrane, the analytes may bind to the surface.

Figure 19:
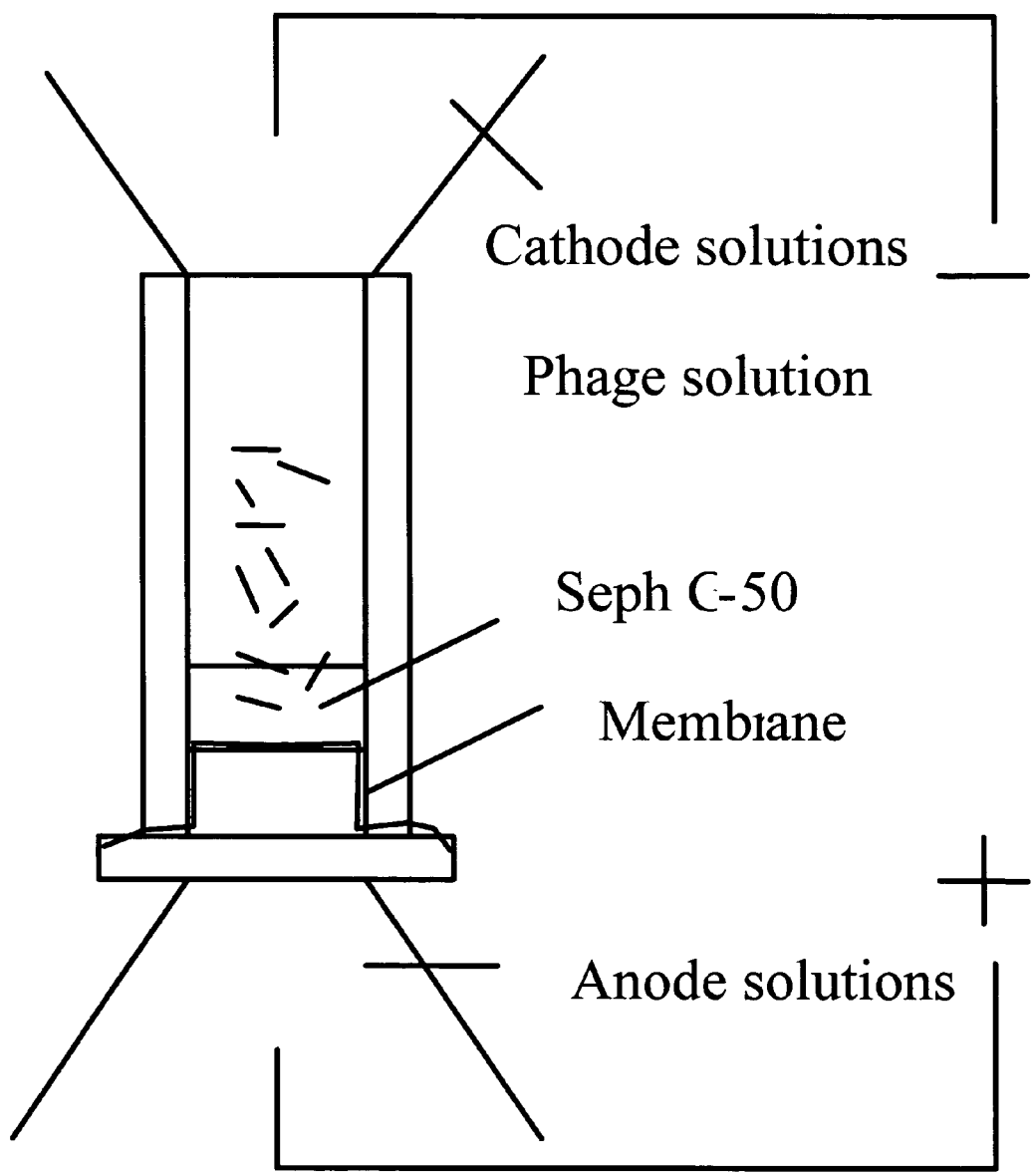
FIG. 19 shows an embodiment of electrophoretic collection of viruses onto a capturing membrane through a layer of Sephadex G-50 preventing a direct contact of virus solution with the capturing membrane.

For example, a lacquered membrane coated with BSA/GA may be treated with 1% PEI solution having a pH of 7.4. As a result of such treatment, a monolayer of a positively charged polymer may be chemically linked to the BSA surface. As illustrated in FIG. 19, negatively charged fd phage particles can be electrophoretically collected on such positively charged surface from a 10 mM acetic buffer with a pH of 4.5 through a 3 mm layer of Sephadex G-50 placed on the lacquered membrane. The layer of Sephadex protected surface from interaction with *E. coli* debris and other impurities present in the phage stock. Electrophoresis was performed for 6 min at 100 V with the positive potential applied to the bottom electrode chamber. The potential was then reversed for 15 sec and returned to the initial direction for 30 sec for an additional 4 min.

AFM images (e.g., twelve 2.1×2.1 $\mu m^2$ images) were taken randomly. Fd phage particles were counted. It was determined that capturing from 0.34 mL of fd phage stock diluted at 1:1,000 on the active membrane with the total area of 36.3 $mm^2$ resulted in a surface density of 0.76±0.1 phages/$\mu m^2$. Taking into account these data, concentration of the phage particles in the stock solution was estimated as $0.8 \times 10^{11}$ phages/mL.

The layer of Sephadex serves as a filtering layer that aids in separating analytes from nonanalytes and other debris, which may constitute noise when detecting and imaging analytes. Sephadex equivalents (e.g., Agarose, Sepharose, Matrex Sellufine, etc.) may also be used as a filtering layer in lieu of Sephadex. Sephadex and Sepharose are trade names for gels that are available commercially in a broad range of porosity. The porosity of the gel can be adjusted to exclude all molecules above a certain size. Matrex Sellufine is also a trade name and a commercially available product.

Besides fd phages, adenoviruses may also serve as analytes and may also be negatively charged at neutral and slightly acidic pH. Similar to the example above, PEI may be used to treat a lacquered membrane to capture adenoviruses. Buffers may be chosen to provide a minimal pH at which analytes can still be stable and keep their negative charge on the surface. Thus, a pH of 4.7 was selected for fd phages, which has approximately 10,000 negative charges at its surface and can strongly adhere to the PEI coated surface. For electrophoretic capturing of adenoviruses, a pH of 6.5 was chosen as a minimal pH at which its capsid can still be stabile.

Figure 17:
FIG. 17 shows fd phages captured on a membrane coated with a layer of BSA/GA and activated by PEI.
Figure 18:
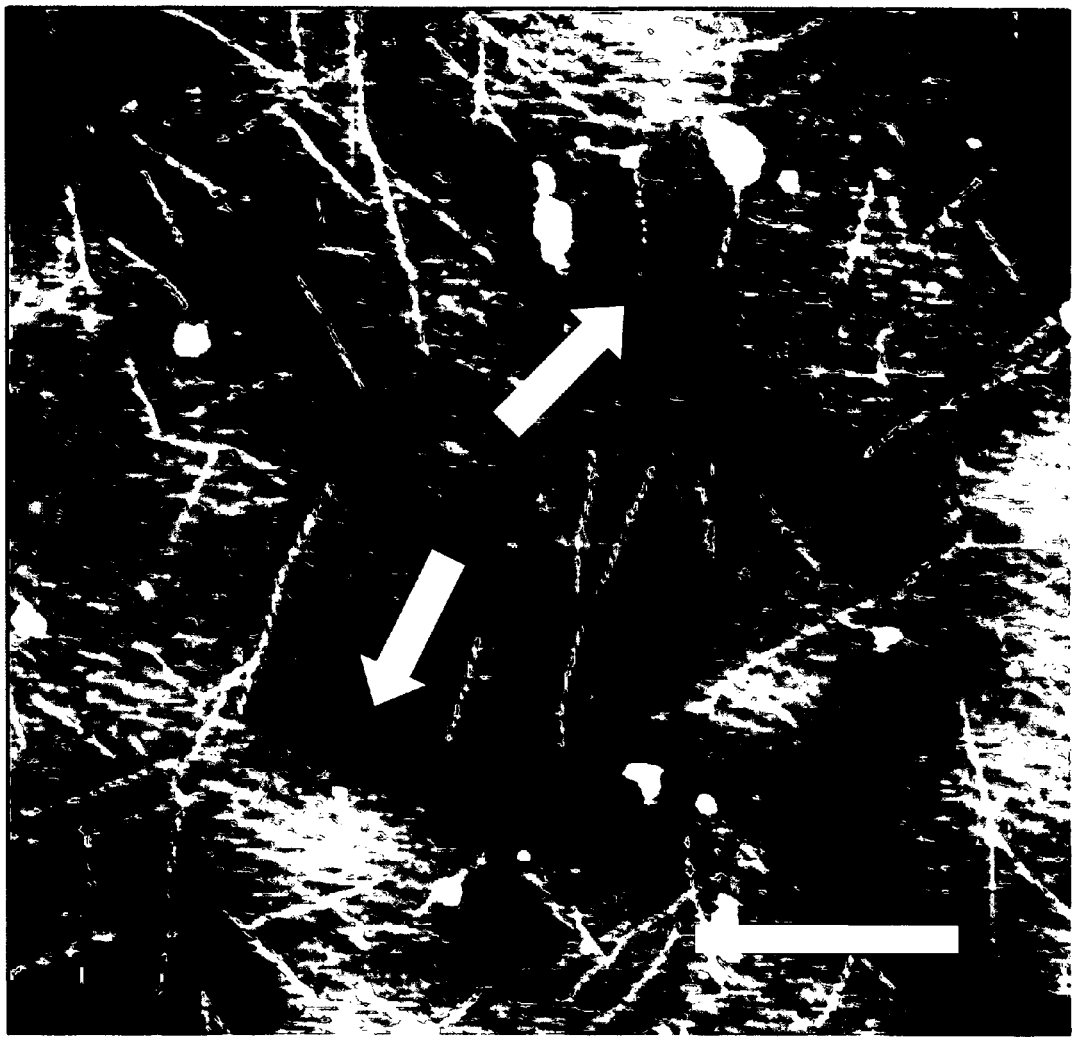
FIG. 18 shows fd phages captured on a membrane coated with a layer of oxidized dextran and activated by PEI.
Figure 20:
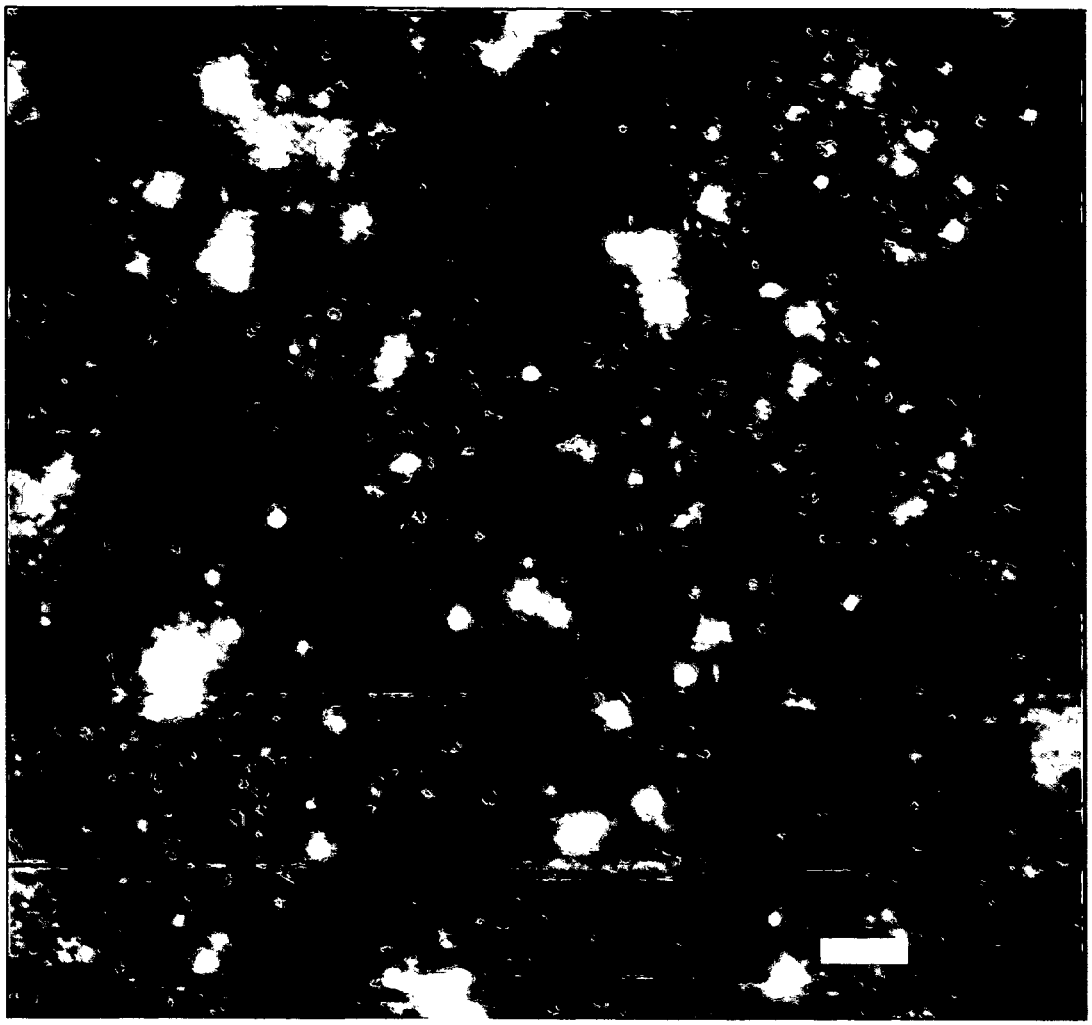
FIG. 20 shows adenoviruses captured on a dextran layer and activated by PEI.
Figure 21:
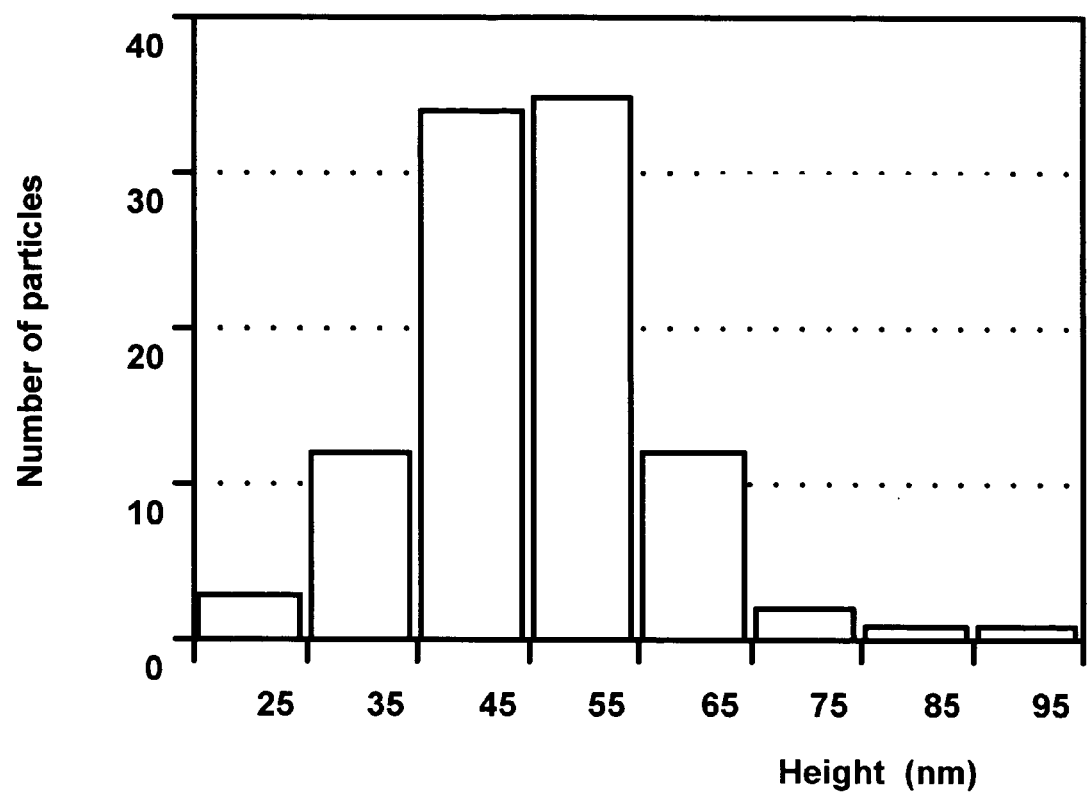
FIG. 21 shows a histogram of the height distribution of adenovirus particles in AFM images.

Images in FIGS. 17 and 18 illustrate fd phages captured on PEI-coated surfaces of BSA/GA and oxidized dextran. Both surfaces were formed in contact with air. Despite the low average height of the phage, 3.4±0.3 nm, it may be readily seen on both lacquered surfaces. The average height of the dry fd phage measured on the polymer surface may correspond to 3.0 nm measured on the solid mica surface at 15% humidity known in the art. Similarly, as seen in FIGS. 20 and 21, the average height of dry adenoviruses on the lacquered surface, H=51±11 nm, fits the average height of the recombinant adenoviruses, H=55 nm, measured by AFM in dry air on a solid silicon substrate. Such a similarity in the height indicate that no substantial part of captured phage and virus is buried into the dextran or BSA layer and that the measured height correspond to those of dry collapsed viral and phage particles only.

Occasionally, bacterial flagella and cell debris may be observed in AFM images, since phage preparations may not be highly purified. These may be readily distinguished from the phage filaments as being much longer (e.g., several micrometers as compared to approximately 0.7 $\mu m$ for fd phages) and notably thicker. Adenoviral particles may be identified by their semispherical shape and their height (between 40 and 60 nm). These particles are predominant in the AFM image on FIG. 20. All other semispherical and non-spherical objects may be considered as impurities.

To remove these impurities, a filtering layer with filtering particles (e.g., Sephadex, Sepharose. Matrex Sellufine, etc.) may be used. After capturing fd phages through a layer of Sephadex, minimal debris may be observed. This effect may might be due to the absence of direct contact of the phage suspension with the membrane and the relatively low pH=4.7 at which capturing was performed. Only negatively charged phages may be able to move through the Sephadex layer toward the membrane under these conditions.

Figure 22:
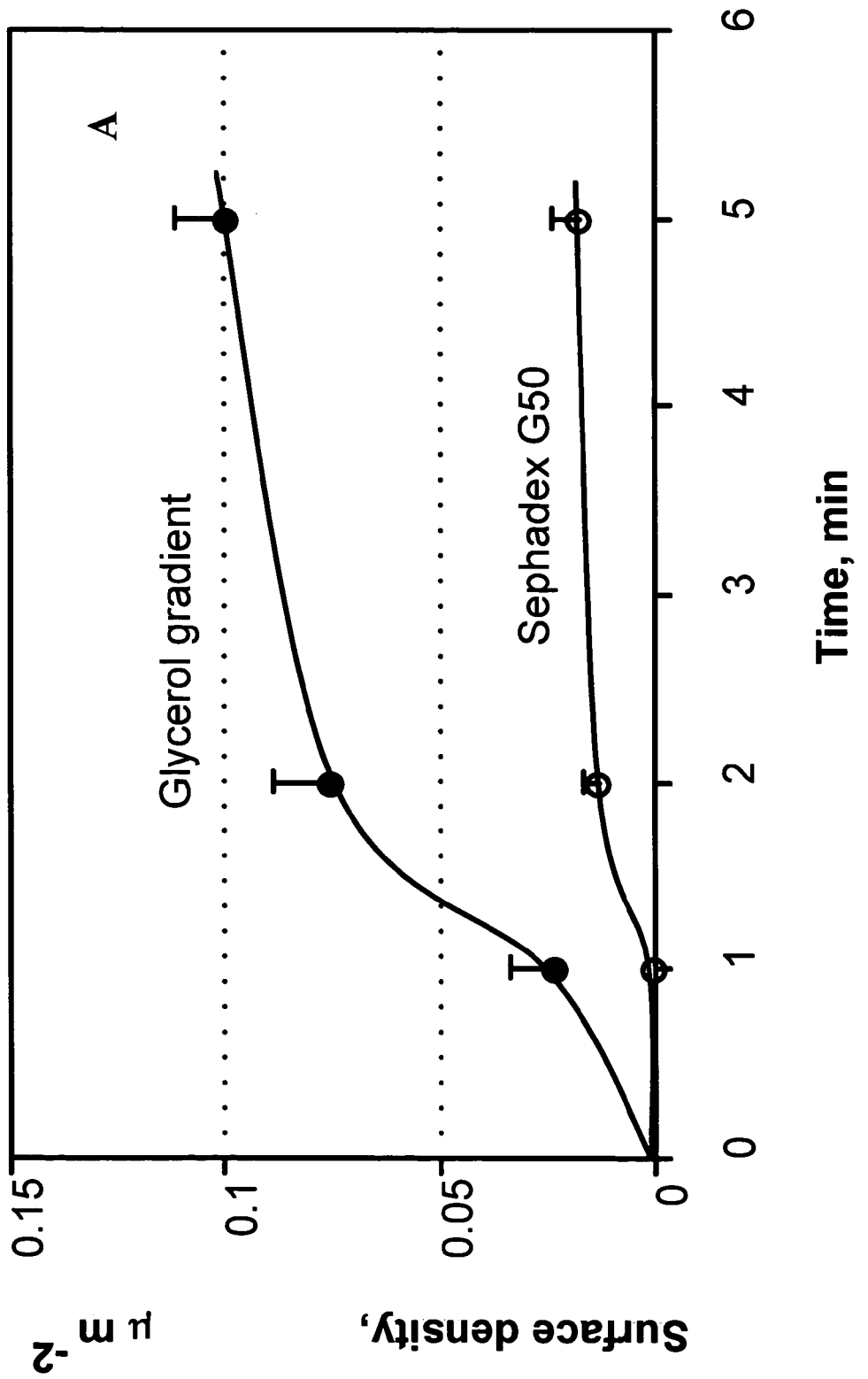
FIG. 22 shows dynamics of adenoviruses capturing through a layer of Sephadex G-50 (empty circles) and in a gradient of glycerol (filled circles).
Figure 23:
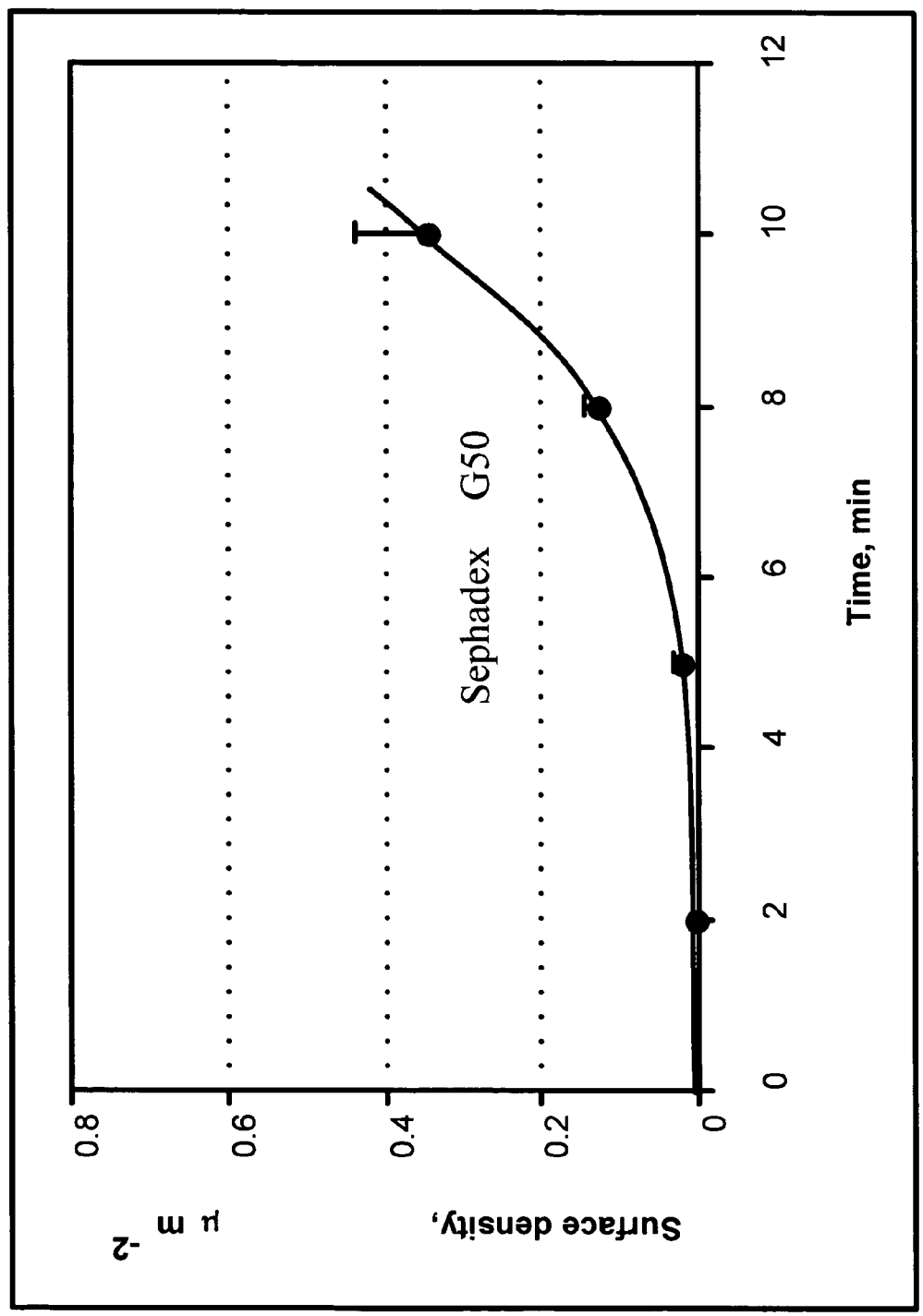
FIG. 23 shows dynamics of fd phages capturing through a layer of Sephadex G-50.

The dynamics of capturing phages and viruses through a layer of Sephadex G-50 may display common features. As seen in FIG. 22, it can take approximately 1 min for adenoviruses to penetrate through the Sephadex layer. Most particles that successfully penetrate can reach the surface in about 5 min. Comparing the two curves in FIG. 22, only 15-20% of viral particles make their way through the Sephadex layer; the rest become trapped in the layer. One can see similar dynamics of capturing fd phages in FIG. 23. The first phages tend to appear on the surface after 5 min of electrophoresis. Their surface density then slowly increases during the next 10 min, indicating a lower mobility of the filamentous phages in the Sephadex layer. Thus, though electrophoresis through the Sephadex layer resulted in more clean samples having less cell debris as compared to the electrophoresis in the glycerol gradient, a substantial amount of viral particles tend to be lost by being trapped in the Sephadex layer.

The surface density of adenoviruses may reach saturation within 5-10 min upon electroconcentration in the glycerol gradient, as seen in FIG. 22. It may happen at low surface coverage, indicating that the saturation is reached not due to the lack of free surface but due to the depletion in the virus suspension. Though a certain amount of viral particles might end up by binding to the walls of the electrophoretic cell, a small diffusion coefficient and a short capturing time make this fraction negligible. Approximately 70% of protein analytes placed into the electrophoretic cell may be found on the lacquered membrane. Since virus particles diffuse slower than protein molecules, and therefore, may be less prone to adsorption onto the walls, they can be collected on the membrane more efficiently. Being charged and subjected to the electric field, viruses tend to have no chance in remaining in solution after electrophoresis. Assuming that in the absence of Sephadex most viral particles are captured on the membrane, one can calculate their total number in the suspension by multiplying average surface density into the total membrane area exposed to electrophoresis. Here, determined concentration of adenoviral particles in stock suspension with $TCID_{50}=1 \times 10^8$ units/mL can be $1.4 \times 10^9$ particles/mL indicating that only one viral particle out of 14 was capable of proliferation. Hence, the combination of active capturing with AFM imaging may allow one to rapidly quantify viability of viral preparation.

It is important to note that electroconcentration may allow the use of a much lower total concentration of fd phages (e.g., approximately $10^8$ particles/mL) and adenoviruses (e.g., approximately $10^6$ particles/mL) as compared to that used in passive capturing of viruses on antibody coated gold ($10^9$ pfu/mL for fd phage and $10^{11}$ adenoviral particles/mL).

After electrocapture, fd phages can be easily detected in images with a field area of s ~50 $\mu m^2$. Assuming that it is practically acceptable to have a minimum of n=1 phage in N=5 images after collection from a V=1 mL sample onto a membrane with a total area of S=36 $mm^2$, one can estimate the minimum virus concentration is on the order of C=nS/

NVs=1.4×10⁵ particles/mL. It is expected that larger viruses, such as vaccinia, can be detected in 100×100 μm scans, and the theoretical limit for such viruses is reduced to approximately 700 particles/mL.

Direct passive adsorption onto mica may not allow one to estimate the number of viral particles in the sample since not all the viruses tend to be adsorbed, and since the viral particles tend to be distributed over the surface non-uniformly. Electrophoretic capturing solves both these problems.

In an example involving adenoviruses, no adenoviruses were found on the substrate after 1 min of electrophoresis. Longer electrophoresis brought virus particles to the surface. Surface density of the bound particles almost reached the saturation after 10 min of capturing in glycerol gradient. With the total active membrane area of 36.3 mm$^2$, it was estimated that stock solution in this example contained 4×10⁸ viral particles/mL. This amount is approximately 4 times higher than the pfu/mL value determined by standard methods in the cell culture.

The following were procedures used: capturing at 180 V and current of 1.5 mA per cell through a layer of Sephadex G-50, 3 mm thick. 0.3 mL of the stock virus solution were diluted 1:100 with 10 mM MES buffer, pH=6.5, 0.1% Tween-20. Voltage–150 V, 1.5 mA/cell. Numbers of viral particles in 5-6 images are averaged.

Figure 24:
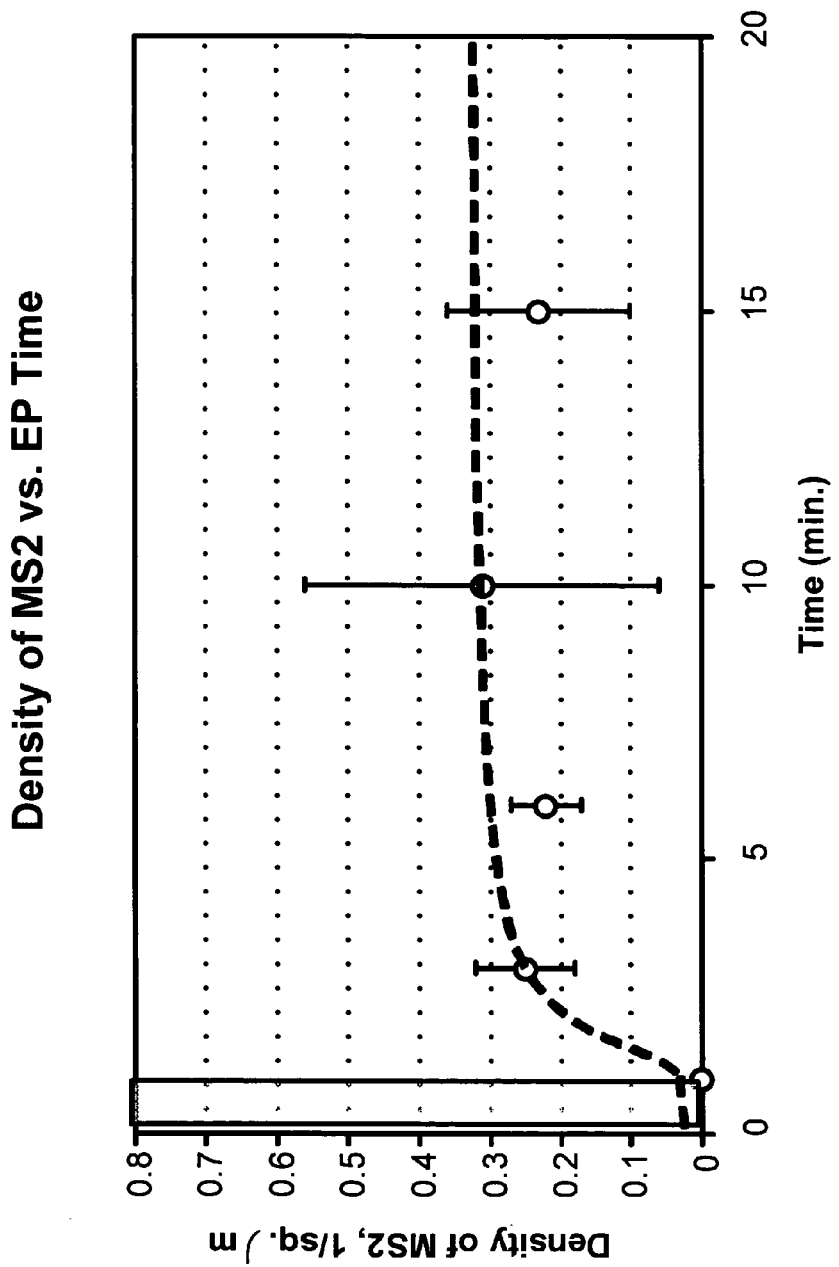
FIG. 24 shows dynamics of capturing MS2 bacteriophages from a solution through a layer of Sepahdex G-50.

In another example, FIG. 24 presents results of capturing of MS-2 bacteriophages under similar conditions. These phages are seen in AFM as dots, 12-15 nm high. It is seen that all MS2 phages are captured within 3 min. The total number of phages in the sample is estimated as (2-3)×10⁹ particles/mL.

In FIG. 24, the procedures used are similar with some modifications. These modifications are: BIS/TRIS buffer, pH=6.6, 0.1% Tween-20. Phage stock is diluted 1:100.

Figure 25:
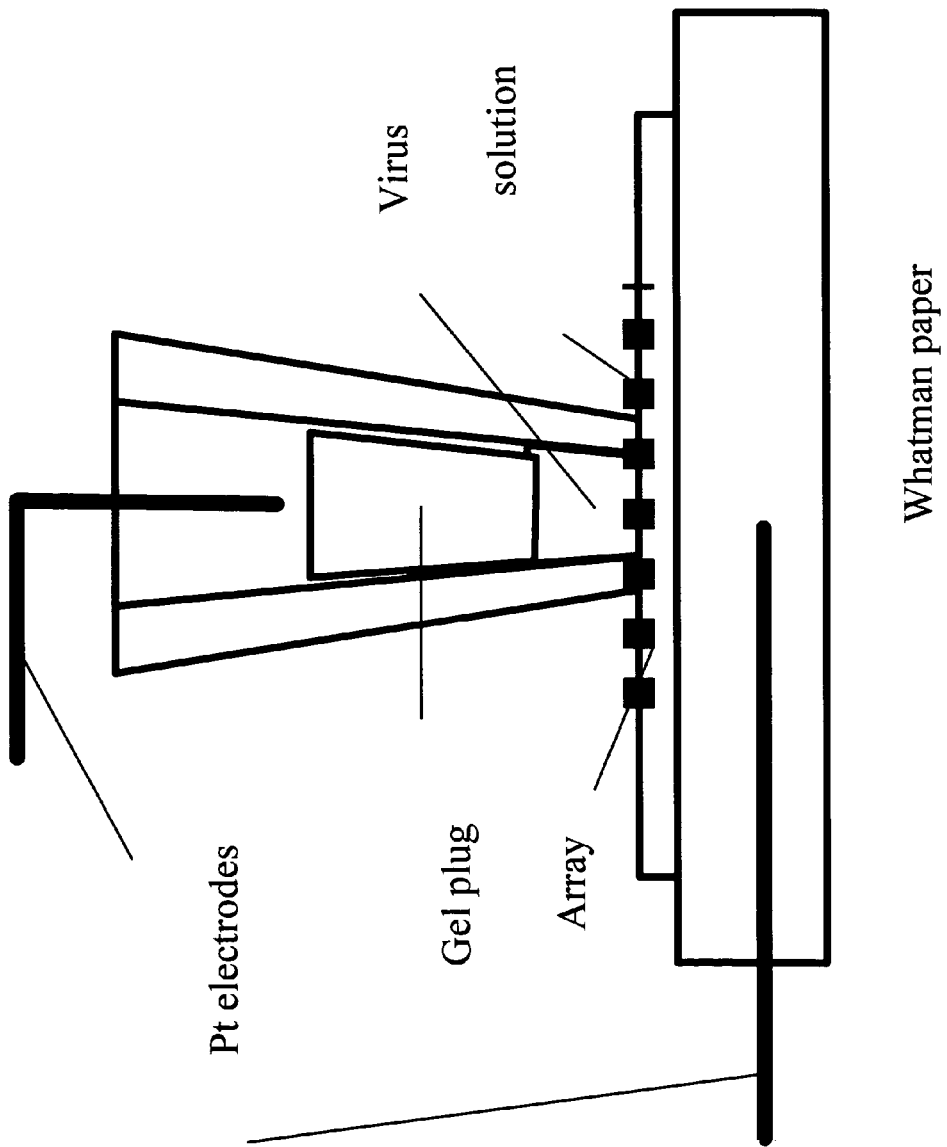
FIG. 25 shows an embodiment of capturing viruses onto a microarray of antibodies from a pipette tip, where the platinum electrode is used to actively deposit viruses by electric field.
Figure 26:
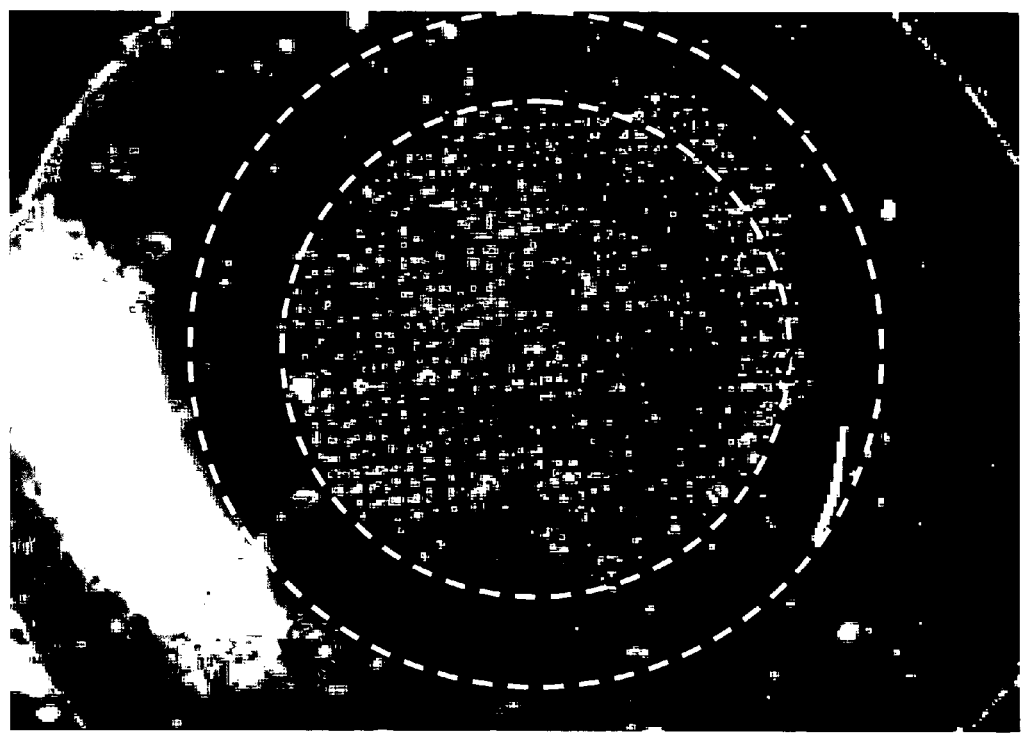
FIG. 26 shows an embodiment of capturing viruses onto a microarray of antibodies from a pipette tip, where beads functionalized with anti-adenovirus antibodies are used to mark the fraction of anti-adeno microarray (inner circle), which contains viruses bound from the pipette.

In yet another example of electrocapturing, analytes may be electrocaptured from a capillary. As depicted in FIG. 25, a negative voltage is applied to a Pt electrode placed inside a pipette and separated from the pipette tip with a gel plug. The pipette tip was filled with a small volume of adenovirus solution (2-3 μL). Negative potential forces negatively charged adenoviruses to move towards an antibody microarray fabricated on a dialysis membrane. The voltage was applied for 3 min. Functionalized beads were pressed to the whole array and then removed by a magnetic field. FIG. 26 clearly demonstrates that only the area under the pipette tip keeps the beads attached.

This technique may be used in rapid preparation samples for microscopy, when viruses and cells should be quickly and fully deposited onto a substrate.

b. Lacquered Membrane with Probe Molecules

Another method of detecting analytes is chemically linking probe molecules (e.g., antibodies, DNA/RNA, oligonucleotides, enzymes, etc.) onto the lacquered membrane.

One way to introduce probe molecules onto the lacquered membrane is by immobilizing and arraying the probe molecules onto the surface of the lacquered membrane.

Take a BSA coated lacquered membrane for example. Though one could expect that glutaraldehyde groups remaining on the BSA surface may provide functionalities for chemically linking antibodies to the membrane surface via amino groups, such surface tends to show a poor ability to bind antibodies. Moreover, such surface tends to be hydrophobic. Its hydrophobicity cannot be removed by blocking in BSA solutions. In view of this, other activation techniques have been tested in this study. Optical density in the direct ELISA was chosen as a probe for quality of coating. The following activation procedures may be employed.

1. BSA/GA: After cross-linking for 30 min in GA vapor membranes were washed overnight in water before coating.
2. BSA/GA+NHS/EDC: Cross-linked membranes were activated for 7 min in a mixture of NHS/EDC (200 mM and 50 mM, respectively), shortly rinsed with water, centrifuged and dried in dry form overnight.
3. BSA/GA+plasma+NHS/EDC: Cross-linked BSA-GA membranes were first treated in plasma discharge for 20 sec, then in NHS/EDC mixture as described above.
4. BSA/GA+plasma+PEI+GA: Cross-linked BSA/GA membranes, treated in plasma discharge for 20 sec were kept for 20 min in 0.2% PEI solution, pH=8.0, washed and treated for another 20 min in 0.1% GA solution prepared on 10 mM phosphate buffer, pH=7.0. The membranes were then washed overnight in water.

Efficiency of different immobilization techniques is presented in Table 3. It is seen that BSA/GA layer by itself may reveal a very low ability to adsorb or chemically bind antibody molecules. Activation of BSA layer with NHS/EDC mixture tends to increase the efficiency of BSA/GA layer by a factor of 220. Treatment of BSA/GA layer with plasma before NHS/EDC activation can raise coating capacity by 24%. Thus, EDC/NHS activation of natural carboxyl groups of BSA molecules and those created as a result of plasma tend to increase coating capacity by a factor of 100-300.

TABLE 3

Comparison of Different Immobilization Techniques Evaluated by Using Direct ELISA

| Method of IgG immobilization | Coating conditions$^a$ | Average OD in direct ELISA$^b$ |
| --- | --- | --- |
| BSA/GA | 50 mM carbonate buffer, pH = 9.5 | 0.003 ± 0.001 |
| BSA/GA + NHS/EDC | 10 mM MES buffer, pH = 6.0 | 0.66 ± 0.12 |
| BSA/GA + plasma + NHS/EDC | 10 mM MES buffer, pH = 6.0 | 0.82 ± 0.11 |
| BSA/GA + plasma + PEI + GA | 50 mM carbonate buffer, pH = 9.5 | 0.15 ± 0.01 |

Coating may be performed overnight at 4° C. from 10 μg/mL of dialyzed rabbit IgG solution in the buffer indicated. ELISA may be performed in the electrophoretic cells by passive binding of anti-(rbt)IgG-AP conjugate diluted 1:1,000 by 3% defatted milk dissolved in 20 mM TRIS/HCl buffer, pH=7.4, containing 0.1% Tween-20. The cells may be stirred for 1 hour. After washing, 150 μL of pNPP solution was added to each cell. The mixture may be stirred until a notable color was developed. For comparison, all optical densities in Table 3 may be calculated with an equal reaction time of 5 min.

Figure 27:
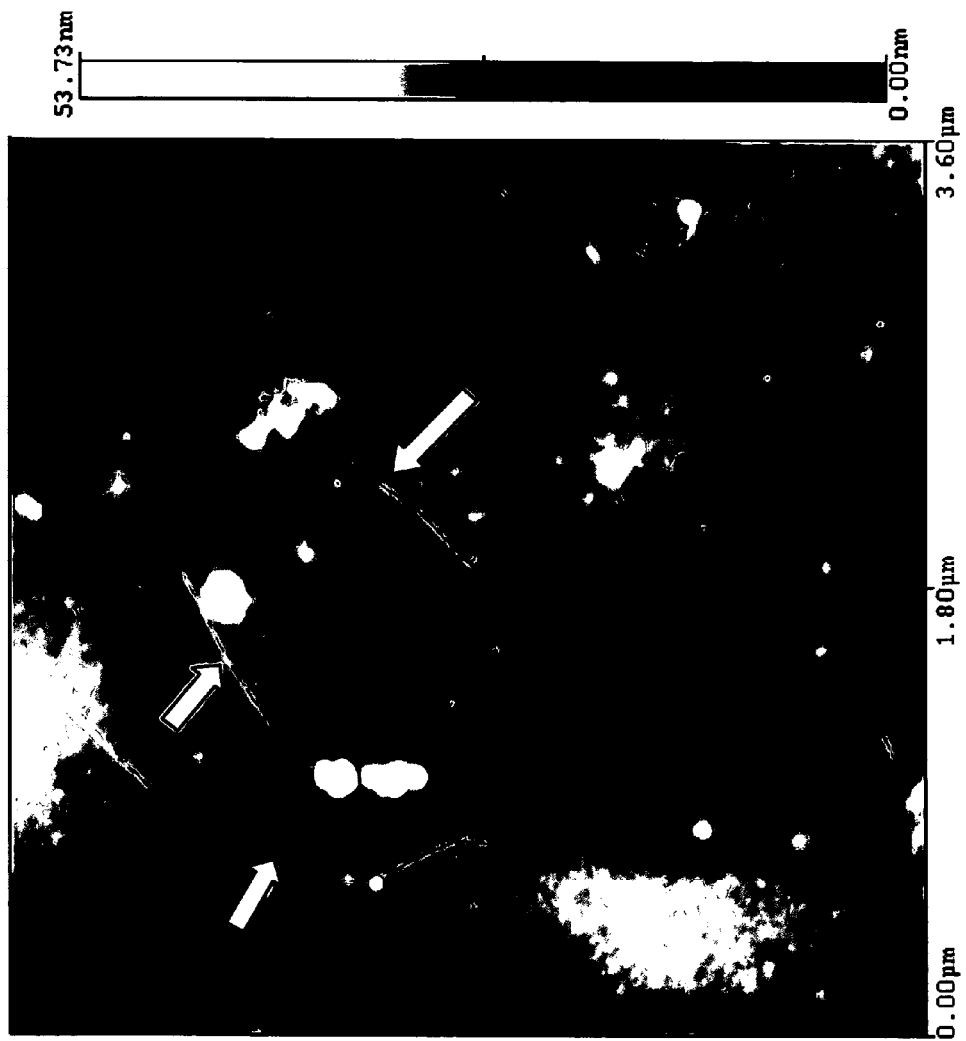
FIG. 27 shows fd phages electrocaptured onto a dialysis membrane coated with BSA layer cross-linked in glutaraldehyde vapor.

As shown in the exemplified FIG. 27, fd phages may be captured on a polyclonal anti-fd-IgG array on a BSA/GA surface. The average height of the fd particles was found to be 3.4±0.4 nm; the average width was found to be 10.6±1.3 nm. This figure represents the first image of filamentous phages on a polymeric surface. All previously published images have been obtained on mica surfaces.

In FIG. 27, the following procedures were used: an array of polyclonal rabbit anti-fd-IgG was electrospray deposited onto BSA/GA surface, linked and blocked by 3% BSA in 0.1 M TRIS/HCl buffer, pH=7.4 containing 0.1% Tween-20. Phages were electrophoretically deposited onto the array surface from 1 mM TRIS/HCl buffer, pH=7.4 at 270 V and 0.3 mA. After electrophoresis array was glued to a glass substrate and dried before AFM imaging in the tapping mode in dry atmosphere.

As for cross-linked oxidized dextran, probe molecules may be deposited onto the lacquered membrane surface using the following exemplified procedures. Deposit a microarray of probe molecules or coat the treated membrane with probe molecules. Buffers containing amino-groups, such as TRIS/HCl, should be avoided. Reduce Schiff' bonds with a solution containing 1% of cyanoborohydride and 1% of BSA for 20 min. Add 0.1 M TRIS/HCl solution to the cyanoborohydride to block the remaining free carbonyls.

Another way of binding probe molecules onto the lacquered membrane is through the use of particles. As one embodiment, probe molecules may be functionalized with particles, in which the particles may be deposited (e.g., epoxy gluing, etc.) onto the lacquered membrane. The particles may be biologically inert polymers. They can also be used as a linker, such as a grafted polymer. Examples of grafted polymers include dextran and polyethylene oxide. Polymer particles are generally separable from the dialysis membrane.

Particles may range in size of at least about 20 nm and no greater than about 20 microns. In particular, many may be at least about 40 nm and no greater than about 10 microns. The particles may be organic or inorganic, swellable or non-swellable, porous or non-porous. Also, they may be suspendible in water. The particles may or may not be electrically charged. Additionally, the particles may be solid particles (e.g., polymer, metal, glass, organic and inorganic (such as minerals, salts and diatoms), etc.), oil droplets (e.g., hydrocarbon, fluorocarbon, silicon fluid), or vesicles (e.g., synthetic assemblies, such as phospholipids, or natural assemblies, such as cells and organelles). Moreover, the particles may also be derived from naturally occurring materials, which may or may not be synthetically modified, or be made of synthetic materials. Furthermore, the particles may be latex particles or other particles comprised of organic or inorganic polymers, lipid bilayers (e.g., liposomes, phospholipid vesicles, etc.), oil droplets, silicon particles, metal sols, cells and dye crystallites.

Organic particles are normally polymers, either addition or condensation polymers, which can be readily dispersible in an assay medium. The organic particles may also be adsorptive or functionalizable so as that an analyte may bind at their surface either directly or indirectly. Examples of organic materials for particles include natural polymers, polysaccharides (e.g., cross-linked polysaccharides, such as agarose, dextran, cellulose, starch, etc.), proteins, and synthetic polymers (e.g., polystyrene, polyacrylamide, homopolymers and copolymers of derivatives of acrylate and methacrylate, particularly esters and amides having free hydroxyl functionalities including hydrogels and the like).

Inorganic particles may include silicones, glasses, and the like.

Sols may include gold, selenium, platinum and other metals.

The particles may be polyfunctional or be capable of being polyfunctionalized. Also, the particles are capable of binding to an analyte or a probe molecule through specific or nonspecific covalent or non-covalent interactions. A plurality of functional groups may be incorporated. Examples include, but are not limited to, carboxylic acids, aldehydes, amino groups, cyano groups, epoxy groups, hydroxyl groups, mercapto groups, etc. When covalent bonding exists, the manner of linking is well known in the art. Linking may depend on numerous factors, such as the nature of the particles, the length of the linker used to bind the probe molecule to the particle, etc.

Comparison of Standard and Active ELISA in Assay of Fd Phages

1. Standard ELISA in Microtiter Plates

NUNC microplates may be coated with anti-fd-IgG (polyclonal, IgG fraction of rabbit serum, purchased from Sigma). A mixture of 50 μL of anti-fd-IgG diluted 100 times with 50 mM carbonate buffer (pH=9.5) was placed in each well and the plate may be kept overnight at 4° C. The wells may then be washed, blocked with 0.5% BSA in PBS and filled with 100 μL of fd phage diluted by the blocking solution. The plate may be intensively stirred for 2 hours at room temperature, washed and filled different dilutions of biotinilated anti-fd-IgG on the same buffer. After intensive stirring, the wells may be washed and filled with streptavidin-AP conjugate diluted 1,000-fold. The plate may be stirred again for 1 hour. After stirring, the plate may be washed. The walls may be filled with 150 μL of pNPP solution. Then, the plate may be stirred again for 45 min. Optical density may be measured at 405 nm using a microplate scanner. As seen from FIG. 28, standard ELISA is capable of measuring phages which are present in more than $1 \times 10^6$ viruses/100 μL (i.e., when virus concentration exceeds $1 \times 10^7$ viruses/mL). Thus, determined sensitivity well tends to correspond to the sensitivity provided by the vendor of the anti-fg-IgG used to design the assay.

2. Electrophoretically Assisted ELISA for fd Phages on Antibody Array

Preliminary data obtained for electrophoretic capturing phages on a microarray of antibodies is described here. Thoroughly dialyzed anti-fd-IgG was electrospray deposited onto BSA/GA coated dialysis membrane from a solution containing 1 mg/mL of antibody and 40 mg/mL of sucrose. Of this solution, 3 μL was electrosprayed though a mesh. The array containing approximately 500,000 spots of dry sucrose/IgG mixture was placed into a Petri dish with 100% humidity for 30 min to immobilize antibodies. The surface was blocked with 1% BSA dissolved in 50 mM TRIS/HCl buffer. Pieces (10×10 mm) of the array were cut and attached into electrophoretic cells schematically presented in FIG. 19. The cells were manufactured from 0.6 mL microcentrifuge tubes by cutting a hole in the caps and by cutting off the conic lower parts of the tubes.

Phages were diluted in 10 mM acetic buffer, pH=4.5, 0.1% Tween-20, and carefully applied on the top of a 2-3 mm layer of Sephadex-50 G equilibrated with the same buffer. Electrophoretic capturing was performed for 6 min at 108-115 V and a current of 1.5 mA/cell (where the positive charge is at the bottom electrolyte chamber). For the following 4 min, polarity was changed so that 15 sec intervals with reversed polarity were followed by 30 sec intervals with the initial polarity. Such alternating was intended to allow phages diffuse over the array surface (e.g., lateral diffusion) in search of immobilized antibodies. One thousand-fold diluted biotinilated anti-fd-IgG was electrophoretically concentrated for 10 min at the membrane from 10 mM Gly-Gly buffer, pH=8.5 for 10 min (where the positive charge is at the bottom). The array was then washed and streptavidin-AP conjugate was electrophoretically concentrated from the same solution under identical conditions. Finally the array was placed into BCIP/NBT solution and kept there for 30 min. Spots density was measured using the SCION program developed at NIH.

Figure 28:
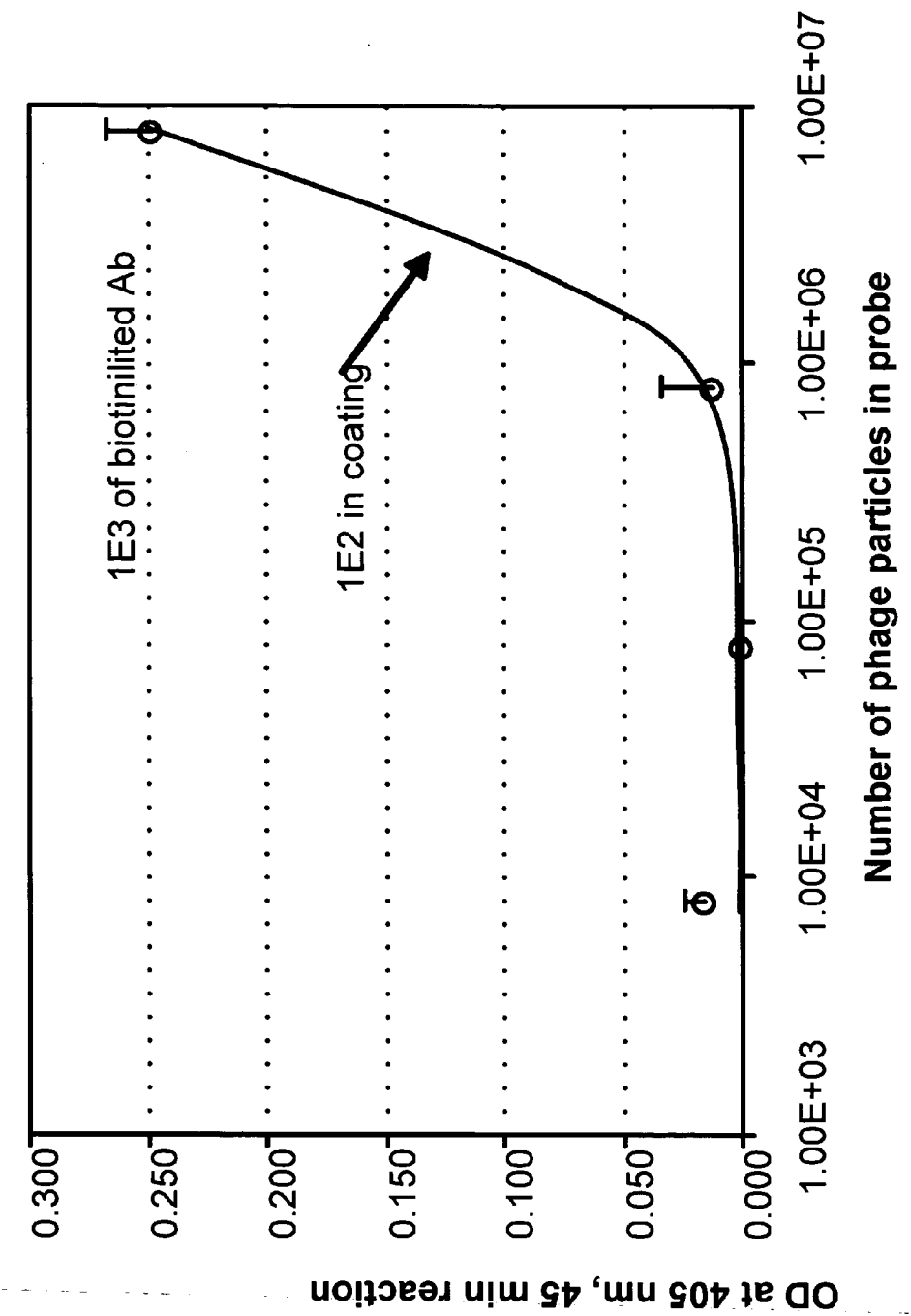
FIG. 28 shows a standard ELISA of fd phage, where the phage was captured on anti-fd-IgG for 2 hour at intensive stirring.
Figure 29:
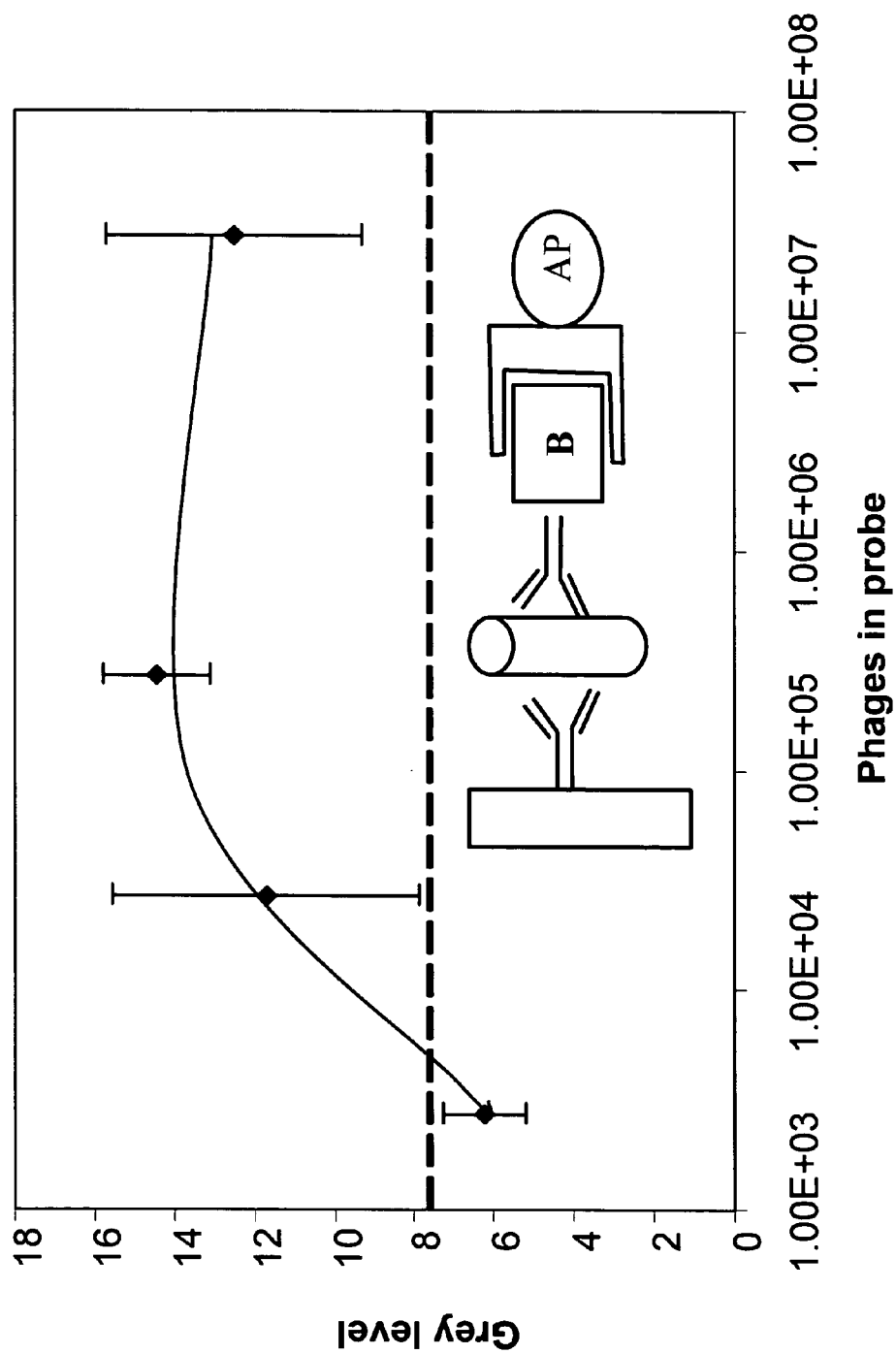
FIG. 29 shows a microarray-based electrophoretically-assisted ELISA of fd phages.

Dependence of spot density as function of a number of phages in the probe of 0.34 mL is presented in FIG. 29. It shows that tens thousands of phages present in the probe results in changes of the density large enough to distinguish them from background. This assay may be performed at the surface (BSA/GA) that may not provide the best immobilization, as one can see from Table 3. The antibody itself may just be an IgG fraction of rabbit serum not subjected to affinity purification. This low quality of commercial antibodies may explain a high level of background noise. Even under such highly unfavorable conditions electrophoretically-assisted ELISA on anti-fd-IgG microarrays may provide approximately a 1000-fold higher sensitivity than the standard ELISA, as shown in FIG. 28.

In FIG. 29, the following procedures were used: Anti-fd-IgG is arrayed. The phages are captured by the anti-fd-IgG spots and labeled first by biotinilated anti-fd-IgG and then by SA-AP conjugate. Distribution and density of AP is measured by optical density of BCIP/NBT product. Dashed line presents background level, when no phage was added to probe.

Another example is to separate recognition and binding on the array. In this scenario, phages may be allowed to react with anti-fd-IgG. In the reaction, the phages may be coated with specific antibody molecules. The combination may be separated from the free molecules and captured on anti-rabbit-IgG array. The last antibody is available in a highly purified form from many manufacturers.

In yet another example, anti-rbt-IgG antibodies may be arrayed on a similar BSA/GA surface. Anti-fd-IgG (prepared in rabbit) may be pre-purified by electrophoresis through a layer of Sephadex G-50 at pH=6.5 as shown in FIG. 19 to remove immunoglobulins with isoelectric point (pI)<6.5. The antibodies with a pI>6.5 collected from the upper part of the electrophoretic cell may be mixed with phages and allowed to react in 10 mM MES buffer with a pH=6.0 for 1 hour. The mixture may then be overlaid on Sephadex layer. Phages negatively charged at this pH may be electrophoretically moved to the anti-rbt-IgG array at the bottom of the electrophoretic cell while positively charged free antibody molecules would not be able to penetrate the Sepadex barrier against the electric field. As a result, phages carrying bound antibodies may be effectively separated from numerous free antibodies. Separation may permit the phages to bind to array spots through rabbit anti-fd-IgG molecules. This procedure may work with unpurified serum and when antibody preparations with a small fraction of phage-specific IgG molecules is used in assay. Comparing FIGS. 30 and 31, the figures show that the last procedure has a slightly larger sensitivity and response intensity.

Figure 30:
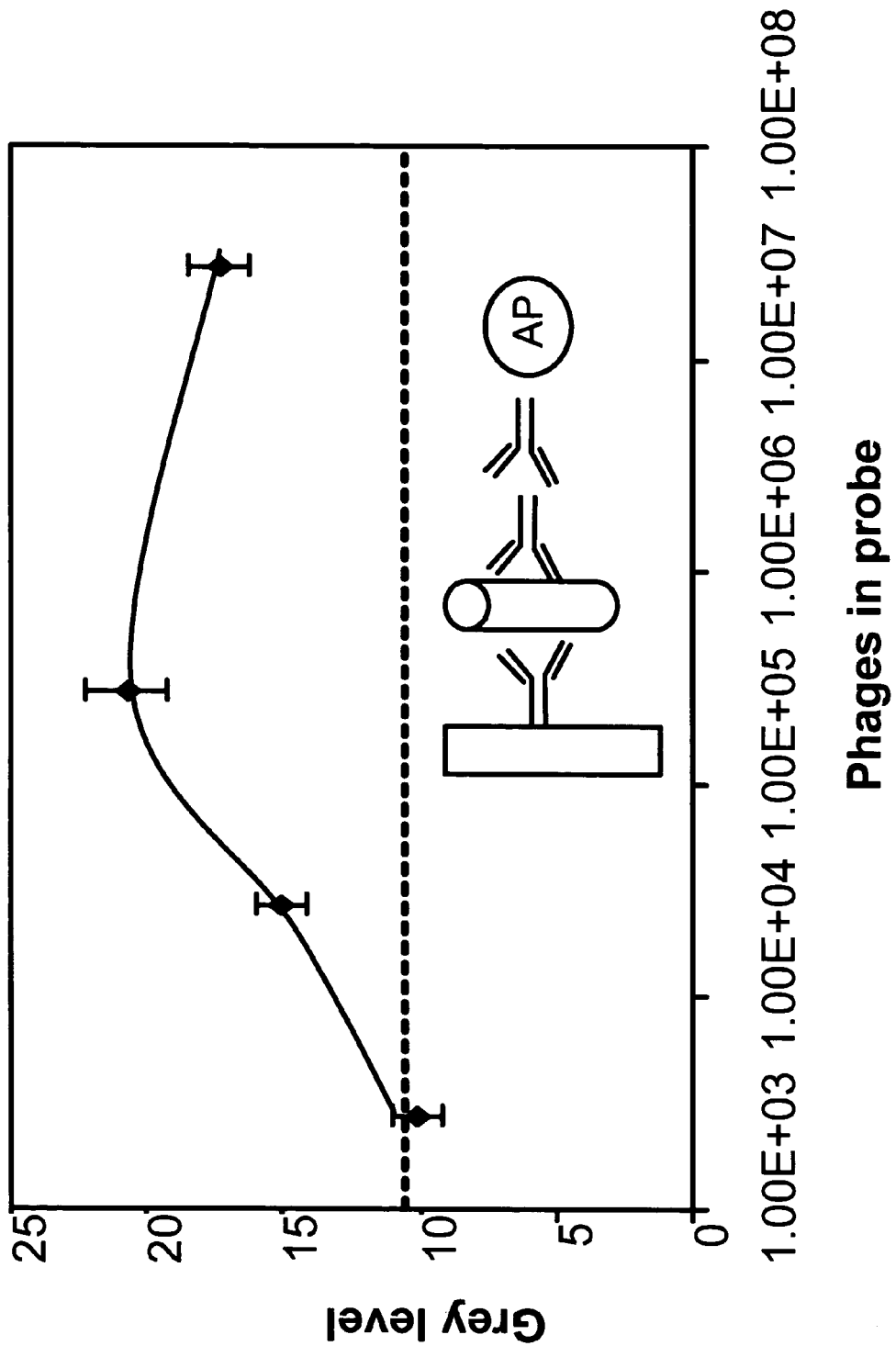
FIG. 30 shows a microarray-based electrophoretically-assisted ELISA of fd phages.

In FIG. 30, the following procedures were used: Anti-rbt-IgG is arrayed. Phages coated by anti-fd-IgG (rabbit) are captured by anti-rbt-IgG spots and detected by biotinilated anti-rbt-IgG-AP conjugate. Distribution and density of AP is measured by density of the BCIP/NBT product.

3. Active Assay in Early Diagnostics

Active assay techniques may be used in early diagnostics of infectious diseases. It is well known that in most cases the first antibody produced in response to a pathogen is immunoglobulin M (IgM). These antibodies may prevail in the serum of infected patients during first days and weeks after a primer infection and may then be progressively replaced by IgG.

Early diagnostics of infection may be critical for further treatment. For example, success of antibiotic treatment of anthrax dramatically decreases as the timing between infection and starting of treatment increases.

In addition to analytes (e.g., pathogens themselves and pathogen-specific antibodies (IgG, IgM, etc.)) other reporters which appear in biological fluids in response to infection should also be considered. The following substances may present avenues for detecting and identifying early infection, while making a prognosis concerning potential progress of the disease: (1) cytokines, which may appear in serum as signaling molecules; (2) alpha and beta interferons; (3) C3 and C5 fragments of the complement system formed upon its activation by bacterial infection; and (4) lethal factor(s) in anthrax and similar products of bacterial metabolism liberated in biological liquids.

The following experimental procedures are suggested to be used for a rapid estimation of these reporter molecules in serum.

a. Procedure for Active Assay for Molecular Reporters

This procedure may include, but is not limited to, the following steps: (1) collecting biological fluid; (2) removing large debris and cells from the fluid by filtration or centrifugation; (3) preparing a sample for electrophoretic capturing using dialysis or electro-dialysis to reduce the content of salt (this step may be combined with the following one); (4) electrocapturing on a microarray, containing probe molecules specifically binding the reporter molecules, such as antibodies against the reporters and major antigens of pathogens; and (5) detecting bound reporters with any available technique, such as ELISA, IFA, RIA, bead detection, etc.

b. Procedure for Active Assay for Traces of Pathogens

This procedure may include, but is not limited to, the following steps: (1) collecting biological fluid; (2) preparing a sample for electrophoretic capturing using dialysis or electro-dialysis to reduce the content of salt; (3) electrocapturing on a microarray, containing antibodies pathogens or other pathogen-specific molecules, e.g., lectins; and (4) detecting bound pathogen cells by direct imaging (optical, electron microscopy, AFM, etc.) or by immune techniques.

Figure 31:
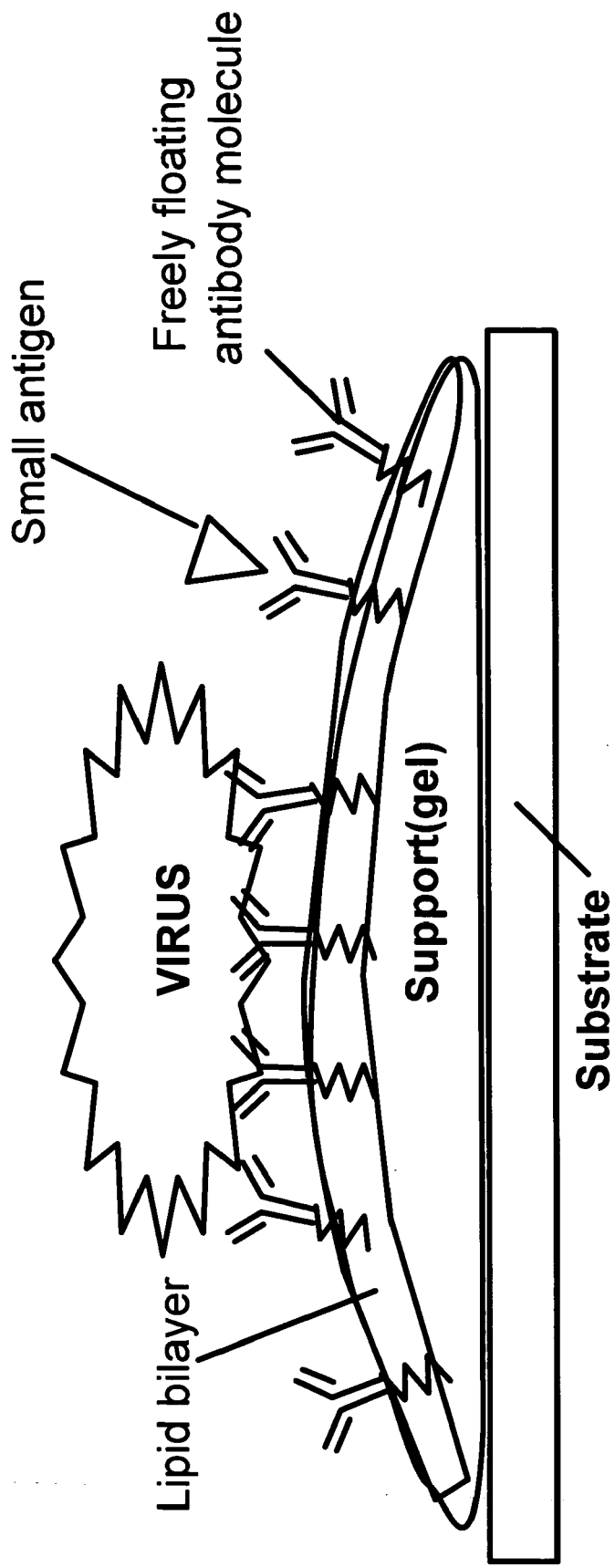
FIG. 31 shows an embodiment of capturing pathogens via a combined action of multiple parallel antibody-antigen bonds.

Specific Capturing Viruses and Cells Via Multiple Parallel Bonds to an Antibody Array Analytes (e.g., viruses and bacteria) may provide multiple sites for interaction with specific molecules. This phenomena can be exploited to increase specificity of pathogen detection in active bioassay. As schematically illustrated in FIG. 31, when allowed to move freely and laterally, antibody molecules are expected to form multiple bonds that may strongly anchor analytes. With the antigen-antibody bond free energy of $\Delta G$, one can expect that cooperative free energy of N bonds breaking in parallel would be $\sim N\Delta G$. The effective binding constant for such polyvalent interaction will be $K_d = (K_d^o)^N$. Thus, even a limited number of relatively weak bonds will hold exceptionally strongly. For example, 3 parallel bonds with $K_d = 10^{-6}$ M each will give the effective binding constant of $(K_d)^3 = 10^{-18}$ M. Even though practically it is difficult to break all the bonds simultaneously, the example shows a great potential of working with parallel bonds. A detailed analysis of polyvalent bonding is presented in Mammen et al, Angew. Chem. Int. Ed. 1998, 37, 2754-2794.

In FIG. 31, antibody probe molecules are freely floated in a lipid bi-layer. Their mobility enables formation of multiple parallel bonds with the antigenic determinants of the pathogen, strongly tethering the latter to the spot. Separate antigens capable of forming only single bond with antibody molecule are unstable and quickly dissociate.

Still, another advantage of the parallel bonding is reduction in interference with other closely related antigens. As illustrated in FIG. 31, the presence of specific antigens, which can only bind a single antibody, is expected to not interfere with the detection of large pathogens. This expectation may be due to weak single antigen-antibody bonds, which may dissociate rapidly upon washing. Another way to reduce the interference is to choose assay conditions far from optimum to allow the formation of weak antigen-antibody bonds. For instance, such conditions include low pH, presence of urea and other denaturation compounds at sub-denaturating concentrations.

Figure 32:
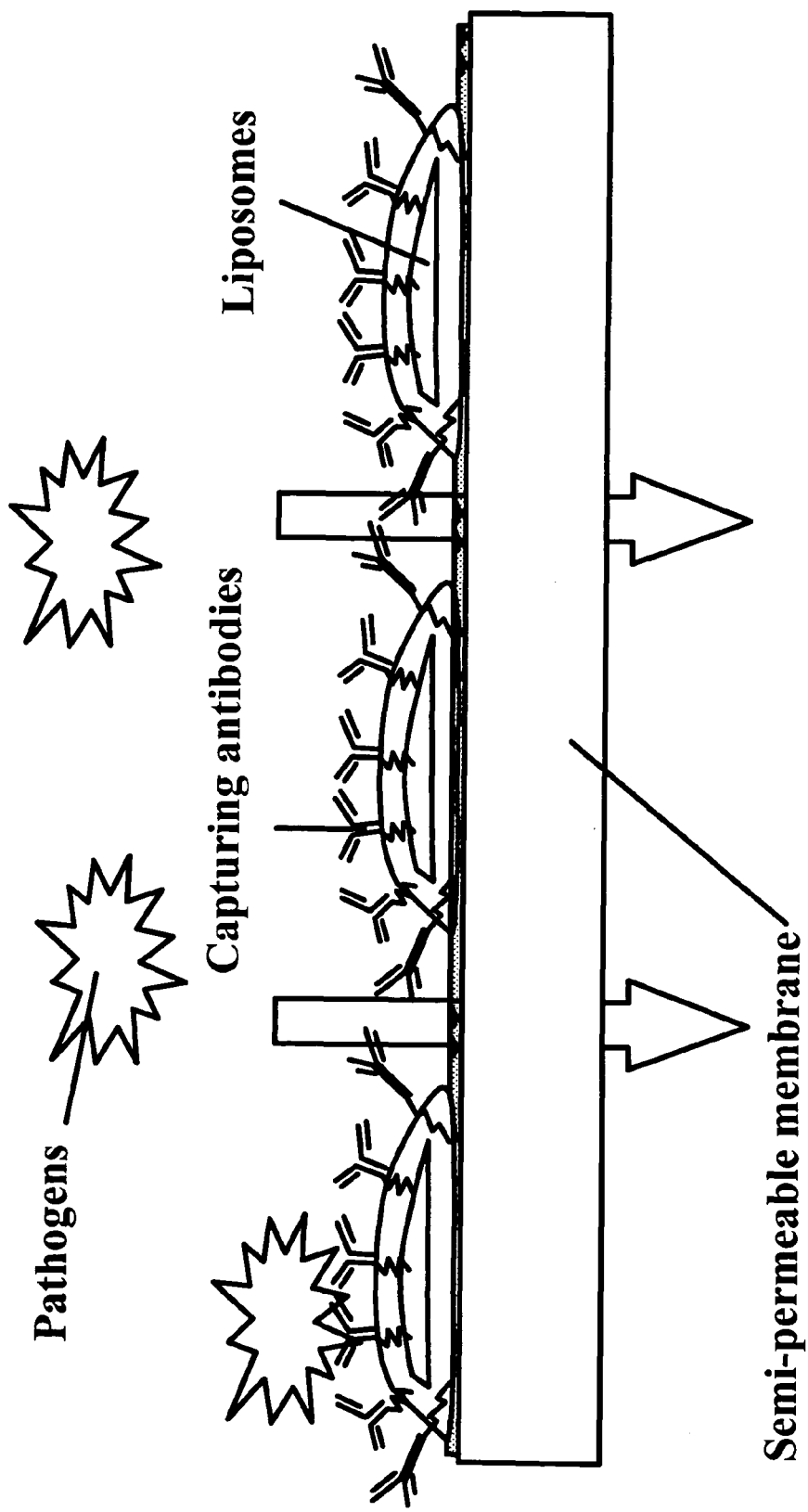
FIG. 32 shows a concept of combining active electrophoretically-assisted capturing of charged pathogens to a microarray comprising of capturing antibodies anchored in liposomes deposited as microarray spots.

Polyvalent bonding may be organized on array. As shown in FIG. 32, antibodies or other probe molecules may be bound to a fluid layer. This fluid layer may be a lipid mono-layer, a lipid bi-layer or an oil layer, supported by a gel substrate, or liposomes adsorbed or chemically bound to a substrate surface. In FIG. 32, arrows visualize motion of salt and buffer ions upon electrophoretic capturing.

Antibodies bound to the substrate surface via long hydrophilic polymer chains can also be used to establish parallel bonds. However, it may be difficult to have antigen-antibody bonds break simultaneously due to the difference in the linker length for different antibody molecules involved in the polyvalent interaction.

The foregoing descriptions of the embodiments of the disclosure have been presented for purposes of illustration and description. They are not intended to be exhaustive or be limiting to the precise forms disclosed, and obviously many modifications and variations are possible in light of the above teaching. The illustrated embodiments were chosen and described in order to best explain the principles of the disclosure and its practical application to thereby enable others skilled in the art to best utilize it in various embodiments and with various modifications as are suited to the particular use contemplated without departing from the spirit and scope of the disclosure. In fact, after reading the above description, it will be apparent to one skilled in the relevant art(s) how to implement the disclosure in alternative embodiments. Thus, the disclosure should not be limited by any of the above described example embodiments. For example, the claimed invention may be practiced over areas near airports, where the cultured cells may consume airport runoff, deicing compounds or pollutant emissions from construction, maintenance or equipment.

In addition, it should be understood that any figures, graphs, tables, examples, etc., which highlight the functionality and advantages of the disclosure, are presented for example purposes only. The architecture of the disclosed is sufficiently flexible and configurable, such that it may be utilized in ways other than that shown. For example, the steps listed in any flowchart may be reordered or only optionally used in some embodiments.

Further, the purpose of the Abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The Abstract is not intended to be limiting as to the scope of the disclosure in any way.

Furthermore, it is the applicants' intent that only claims that include the express language "means for" or "step for" be interpreted under 35 U.S.C. §112, paragraph 6. Claims that do not expressly include the phrase "means for" or "step for" are not to be interpreted under 35 U.S.C. §112, paragraph 6.

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

What is claimed is:

1. A method for detecting an analyte using an active assay comprising:
   a. introducing an analyte solution containing a plurality of analytes to a lacquered membrane, said lacquered membrane:
      i. being a semi-permeable membrane with at least one surface coated with a layer of polymers, forming a lacquered layer;
      ii. having a plurality of probe molecules immobilized on said lacquered layer; and
      iii. being electrically conductive;
   b. capturing said analytes by:
      i. applying an external force to said analytes to move said analytes towards said lacquered layer, thereby allowing some of said analytes to bind onto said probe molecules; and
      ii. reversing the direction of said external force to remove said analytes that are unbound or weakly bound;
   c. detecting said analytes left bound to said probe molecules or said lacquered layer; and
   d. wherein said probe molecules are anchored on said surface using particles in a way that allows said probe molecules to freely float on said particles, said particles having at least one fluid layer.

2. The method according to claim 1, wherein said lacquered layer is made of cross-linked water-soluble polymers.

3. The method according to claim 1, wherein said lacquered membrane is treated with an activation measure.

4. The method according to claim 1, further including a filtering layer, wherein the filtering layer electrophoretically separates said analytes that are charged from nonanalytes and debris.

5. The method according to claim 1, further including periodically changing the direction of said external force to allow lateral diffusion of said analytes.

6. The method according to claim 1, wherein said surface that is coated has a roughness of less than about 2 nm.

7. The method according to claim 1, further including labeling said analytes with a plurality of markers, creating marker-analyte complexes.

8. The method according to claim 7, wherein said probe molecules are specific to said markers.

9. The method according to claim 7, wherein said reversing the direction of said external force further removes and separates said markers from said marker-analyte complexes.

10. The method according to claim 1, wherein said lacquered membrane is permeable to nonanalytes but not to the analytes.

11. The method according to claim 1, wherein said fluid layer is:
    a. at least one of the following:
       i. a lipid mono-layer;
       ii. a lipid bi-layer; and
       iii. an oil layer; and
    b. arrayed on said lacquered membrane.

12. The method according to claim 1, wherein said analytes are biological entities.

* * * * *